United States Patent
Faham et al.

(10) Patent No.: US 7,510,829 B2
(45) Date of Patent: Mar. 31, 2009

(54) MULTIPLEX PCR

(75) Inventors: Malek Faham, Pacifica, CA (US); Eugeni Anatolyevich Namsaraev, Menlo Park, CA (US); Thomas Daniel Willis, San Francisco, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 10/300,285

(22) Filed: Nov. 19, 2002

(65) Prior Publication Data

US 2003/0104459 A1 Jun. 5, 2003

Related U.S. Application Data

(60) Provisional application No. 60/331,693, filed on Nov. 19, 2001.

(51) Int. Cl.
- *C12Q 1/68* (2006.01)
- *C12P 19/34* (2006.01)
- *C07H 21/04* (2006.01)

(52) U.S. Cl. .................. 435/6; 435/91.2; 536/23.1; 536/24.31; 536/24.32; 536/24.33

(58) Field of Classification Search .............. 435/6, 435/91.2; 536/24.33, 24.31, 24.32, 22.1, 536/23.1

See application file for complete search history.

(56) References Cited

U.S. PATENT DOCUMENTS

| | | | |
|---|---|---|---|
| 4,945,051 A | 7/1990 | Kikuchi et al. | |
| 5,185,243 A | 2/1993 | Ullman | 435/6 |
| 5,439,793 A | 8/1995 | Rose | 435/6 |
| 5,491,063 A | 2/1996 | Fisher et al. | |
| 5,508,178 A | 4/1996 | Rose | 435/91.1 |
| 5,525,494 A | 6/1996 | Newton | |
| 5,565,340 A | 10/1996 | Chenchik et al. | |
| 5,582,989 A | 12/1996 | Caskey et al. | |
| 5,595,891 A | 1/1997 | Rose | 435/91.5 |
| 5,612,199 A * | 3/1997 | Western et al. | 435/91.1 |
| 5,728,526 A | 3/1998 | George, Jr. et al. | |
| 5,731,171 A | 3/1998 | Bohlander | |
| 5,851,770 A * | 12/1998 | Babon et al. | 435/6 |
| 5,882,856 A | 3/1999 | Shuber | |
| 5,888,731 A | 3/1999 | Yager et al. | |
| 5,928,905 A | 7/1999 | Stemmer et al. | |
| 5,952,176 A * | 9/1999 | McCarthy et al. | 435/6 |
| 6,045,994 A | 4/2000 | Zabeau et al. | |
| 6,117,679 A * | 9/2000 | Stemmer | 435/6 |
| 6,130,073 A | 10/2000 | Eggerding | |
| 6,150,516 A | 11/2000 | Brenner et al. | |
| 6,207,372 B1 | 3/2001 | Shuber | |
| 6,207,424 B1 | 3/2001 | Chou et al. | |
| 6,326,145 B1 * | 12/2001 | Whitcombe et al. | 435/6 |
| 6,350,580 B1 | 2/2002 | Sorge | |
| 6,355,422 B1 | 3/2002 | Liu et al. | |
| 6,361,942 B1 | 3/2002 | Coull et al. | |
| 6,410,278 B1 * | 6/2002 | Notomi et al. | 435/91.2 |
| 6,949,633 B1 * | 9/2005 | Monforte et al. | 536/22.1 |
| 2001/0049125 A1 | 12/2001 | Stemmer et al. | |
| 2002/0102591 A1 | 8/2002 | Sorge | |
| 2002/0119448 A1 | 8/2002 | Sorge et al. | |
| 2002/0137036 A1 | 9/2002 | Sorge et al. | |
| 2003/0096291 A1 | 5/2003 | Faham et al. | |
| 2003/0104459 A1 | 6/2003 | Faham et al. | |
| 2004/0224352 A1 | 11/2004 | Fan et al. | |

FOREIGN PATENT DOCUMENTS

| | | |
|---|---|---|
| EP | 0799897 | 10/1997 |
| EP | 0971 039 A | 1/2000 |
| WO | WO 96/33207 | 10/1996 |
| WO | WO 96/41012 | 12/1996 |
| WO | WO-97/45559 | 12/1997 |
| WO | WO 99/49293 | 9/1999 |
| WO | WO 99/66071 | 12/1999 |
| WO | WO 0028082 A1 * | 5/2000 |
| WO | WO-01/06012 A1 | 1/2001 |
| WO | WO 01/32922 | 5/2001 |
| WO | WO 01/38558 | 5/2001 |
| WO | WO 01/94625 | 12/2001 |
| WO | WO 02/29112 | 4/2002 |
| WO | WO 02/36821 | 5/2002 |

(Continued)

OTHER PUBLICATIONS

Kebelmann-Betzing et al., "Advantages of a New *Taq* DNA Polymerase in Multiplex PCR and Time-Release PCR," *Biotechniques* vol. 24 No. 1: pp. 154-158 (1998).

(Continued)

*Primary Examiner*—Suryaprabha Chunduru
(74) *Attorney, Agent, or Firm*—Sandra E. Wells

(57) ABSTRACT

Compositions and methods for nucleic acid amplification are provided that minimize the formation and amplification of spurious products, particularly in multiplex amplification reactions. Linear amplification molecules are provided. A first embodiment comprises a first common primer sequence, a first template homology region, a cleavable site, a second common primer sequence and a second template homology region. Methods employing the linear amplification molecules for nucleic acid amplification are also provided. A first embodiment comprises a template-specific hybridization, a linear amplification, a template-specific intramolecular hybridization, a strand cleavage, a second linear amplification and an exponential amplification using common primers.

31 Claims, 16 Drawing Sheets

FOREIGN PATENT DOCUMENTS

| WO | WO 02/59354 | 8/2002 |
|---|---|---|
| WO | WO 02/59355 | 8/2002 |
| WO | WO 02/70751 | 9/2002 |

OTHER PUBLICATIONS

Brookes et al., "Cloning the Shared Components of Complex DNA Resources," *Human Molecular Genetics* vol. 3 No. 11: pp. 2011-2017 (1994).

Markoulatos et al., "Multiplex Polymerase Chain Reaction: A Practical Approach," *J. Clin. Lab. Anal.* vol. 16: pp. 47-51 (2002).

Brownie, J. et al. "The elimination of primer-dimer accumulation in PCR" Nuc. Acids Res., Oxford University Press, vol. 25, No. 16, 3235-3241 (1997).

Peale, F. et al. "Multiplex display polymerase chain reaction amplifies and resolves related sequences sharing a single moderately conserved domain" Anal. Biochem. vol. 256, No. 2, 158-168, (1998).

Broude, N. E., "Stem-loop oligonucleotides: a robust tool for molecular biology and biotechnology," Trends in Biotechnol. 20-6:249-256, (2002).

Baskeran et al., "Uniform Amplification of a Mixture of Deoxyribonucleic Acids with Varying GC Content," *Genome Research* vol. 6 no. 7: pp. 633-638 (Jul. 1998).

Broude et al., "Multiplex Allele-Specific Target Amplification Based on PCR Suppression," *Proclamation of the National Academy of Sciences of the USA* vol. 98: pp. 206-211 (2001).

Chamberlain et al., "Delationa Screening of the Duchenne Muscular Dystrophy Locus via Multiplex DNA Amplification," *Nucleic Acids Research* vol. 16 no. 23: pp. 11141-11156 (1988).

Eurogenetic, *Quantitative and Qualitive PCR Technology: All Types of Probes and Related Expertise In One Company*: pp. 1-47 (2002).

Fan et al., "Parallel Genotyping of Human SNPs Using Generic High-Density Oligonucleotide Tag Arrays," *Genome Research* vol. 10: pp. 853-860 (2000).

Henegariu et al., "Multiplex PCR: Critical Parameters and Step-by-Step Protocol," *Biotechniques* vol. 23 no. 3: pp. 504-511 (Sep. 1997).

http://www4.amershamblosciences.com/aptrix/upp01077.nsf/Content/gel_blot_fluor_Imaging.html "Multiplex PCR Product Analysis: Increased Accuracy and Throughput," (Oct. 31, 2002).

http://www.bu.edu/research/Features/sciocoalltion_01/twist.html "A New Twist on a Powerful Theme," (Oct. 31, 2002).

http://www.bu.edu/research/Features/sciocoalition_01/twist2.html "Return to a New Twist," (Oct. 31, 2002).

http://www.dxsgenotyping.com/technology_main.htm "Sorpions™ Technology for PCR Analysis," (Oct. 31, 2002).

http://www.eurogentec.be/code/en/thec_neal_scor.htm "Scorpions™ Genomics Ollgonucleotides Synthesis," (Oct. 31, 2002).

http://www.info.med.yale.edu/genetics/ward/tavl/guide.html "PCR and Multiplex PCR Guide," (Oct. 31, 2002).

http://www.info.med.yale.edu/genetics/ward/tavi/p01.html "PCR Geheralities," (Oct. 31, 2002).

http://www.info.med.yale.edu/genetics/ward/tavi/p02.html "Choosing/Designing PCR Primers." (Oct. 31, 2002).

http;www.info.med.yale.edu/genetics/ward/tavi/p04.html "Multiplexing Primer Pairs," (Oct. 31, 2002).

http;//www.mdlab.com/fees&servs/serv-polymerase.html "Medical Diagnostic Laboratories Diagnostic Services: Application of the Polymerase Chain Methodologies in Molecular Diiagnostic Medicine, " (Oct. 31, 2002).

http://www.medprobe.com/no/rtper.html "MedProber: Real Time PCR Products and Instruments," (Oct. 31, 2002).

http://www.giagen.com/clinical/applications/technologies/multiplex_pcr.asp "Molecular Diagnostics Research and Clinical Research," (Oct. 31, 2002).

Shoemaker et al., "Quantitative Phenotypic Analysis of Yeast Deletion Mutants Using a Highly Parallel Molecular Bar-Coding Strategy," *Nature Genetics* vol. 14 no. 4: pp. 450-456 (1996).

Tatusova et al., "Blast 2 Sequences - A New Tool for Comparing Protein and Nucleotide Sequences," *FEMS Microbiology Letters* vol. 174: pp. 247-250 (1999).

Thalwall et al., "Mode of Action and Application of Scorpion Primars to Mutation Detection," *Nucleic Acids Research* vol. 28 no. 19: pp. 3752-3761 (2000).

Whitcombe et al., "Detection of PCR Products Using Self-Probing Amplicons and Fluorescenca," *Nature Biotechnology* vol. 17: pp. 804-807 (Aug. 1999).

Zangenberg et al., "Improved Multiplex PCR of Plymorphic Markers," http://www.promega.com/geneticidproc/ussymp7proc/ab73.html (Oct. 31, 2002).

\* cited by examiner

Cleavage of Loopback structure at X

Figure 2B

Opening Loopback structure
after cleavage

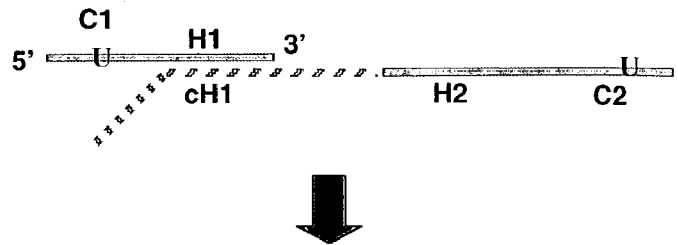

Second DNA synthesis with DNA polymerase able to synthesize through uracil

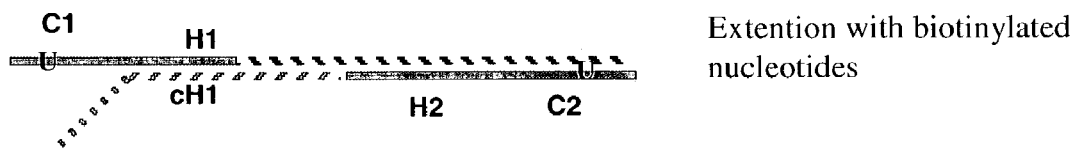

Extention with biotinylated
nucleotides

Streptavidin capture

DNA synthesis with C2 common primer and DNA polymerase
able to synthesize through uracil

PCR with 2 common primers and Pfu DNA polymerase

No remaining probe
dimer will be extended
by Pfu

Annealing probe to DNA or RNA template

First DNA synthesis

Loopback structure formation

Denaturation and renaturation

Remove 3'-overhanging end of new synthesized strand with Exonuclease I

Second DNA synthesis

PCR with C1 primer and complementary primer cC1

Annealing probe to DNA or RNA template and first DNA synthesis

Cleavage of "loopback" structure

Structure 2B

Cleavage by removing uracil with UDG with treatment by AP endonucleases or AP lyases Structure 2A Second DNA synthesis after cleavage Structure 2B Hybridized 3' end of H1 duplex is extended by DNA synthesis Structure 2A Before extention, 3' ssDNA tail is removed by ExoI or 3'-5' exonuclease activity of DNA polymerase "Barcode" (Bc) sequence between C1 and H1 sequences Loopback Probe Processing ⬇

PCR product

"Barcode" (Bc) sequence between C2 and H2 sequences

Loopback Probe

Processing ⬇

PCR product

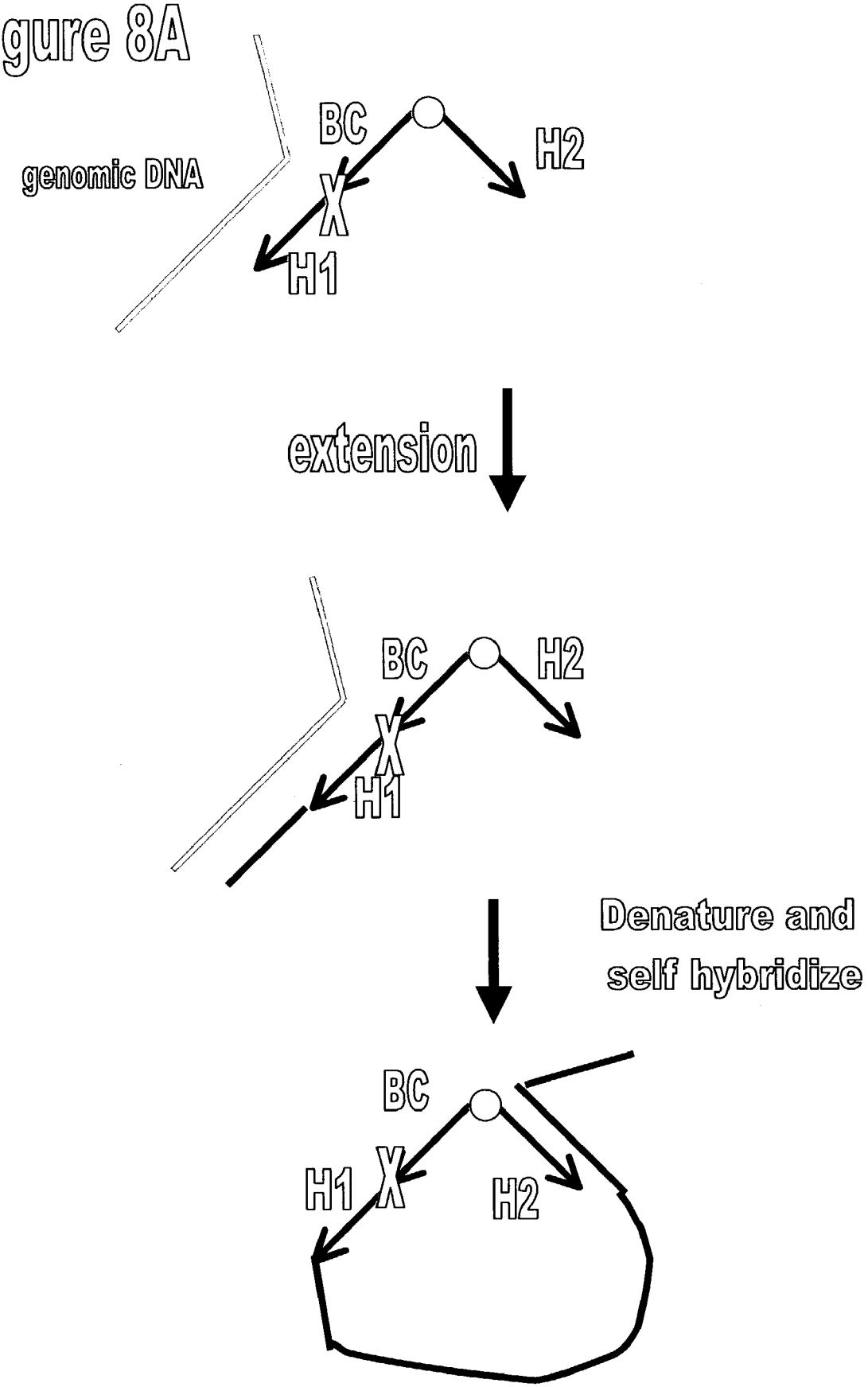

↓ Extension

↓ Nick and denature

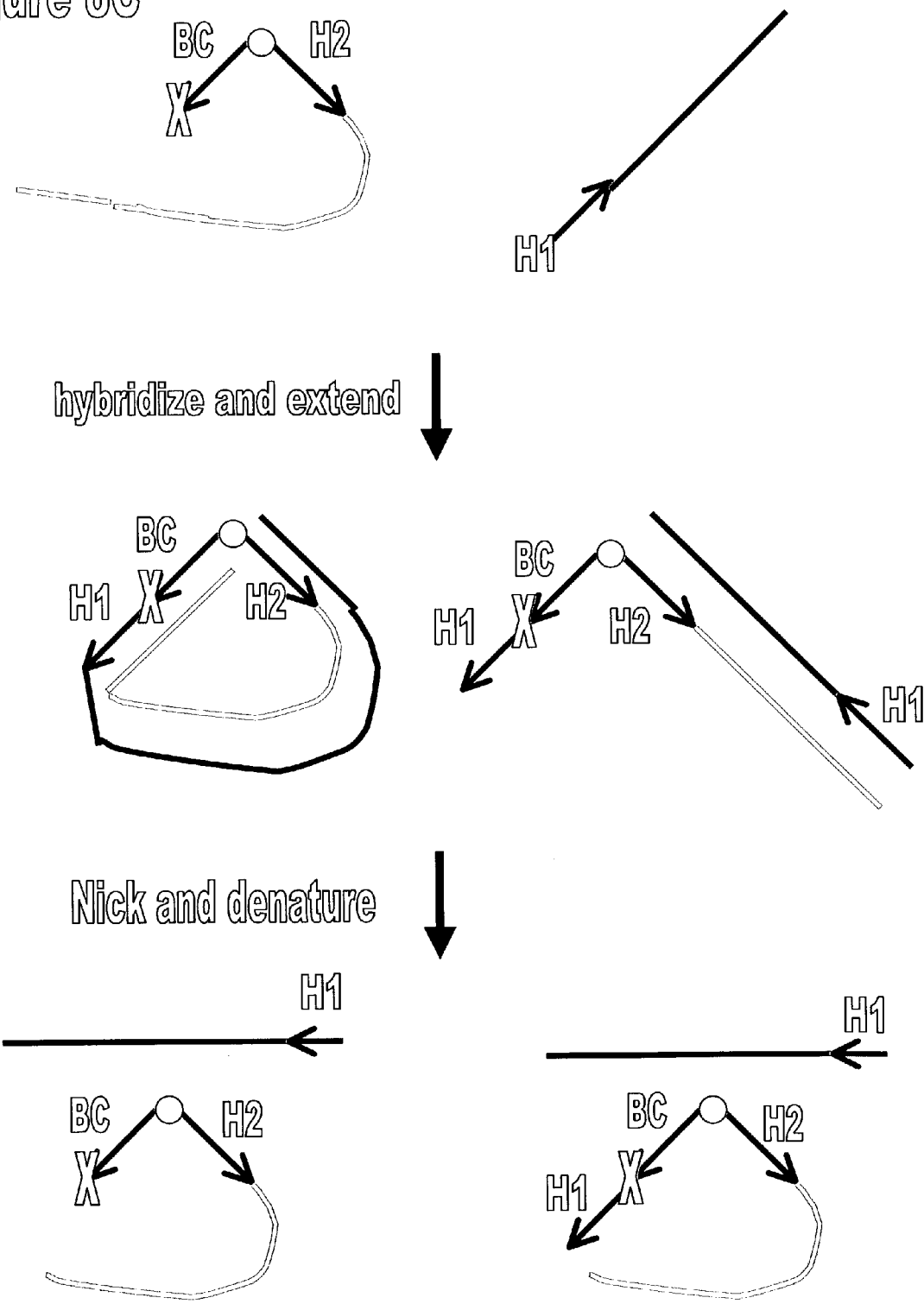

```
                      SEQUENCE LISTING

<160> NUMBER OF SEQ ID NOS: 10

<210> SEQ ID NO 1
<211> LENGTH: 130
<212> TYPE: DNA
<213> ORGANISM: Artificial Sequence
<220> FEATURE:
<223> OTHER INFORMATION: Description of Artificial Sequence: Synthetic
      DNA/RNA sequence
<220> FEATURE:
<223> OTHER INFORMATION: Description of Combined DNA/RNA Molecule:
      Synthetic DNA/RNA sequence

<400> SEQUENCE: 1
ttgtcgaaca gtccacgagg tctctagtcc gaattgtttc atcatcgtta uuacgtagct      60
gtaaaacgtc ggccagtgct attcgctgga gttcgcacgc tatatttaaa agcatcacca    120
gaagaaacag                                                            130

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtccacgagg tctctagtc                                                   19

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tgtaaaacgt cggccagtgc tattc                                            25

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 4
cgaattgttt catcatcgtt a                                        21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
agcatcacca gaagaaacag                                          20

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cgaattgttt catcatcgtt actgtttctt ctggtgatgc t                  41

<210> SEQ ID NO 7
<211> LENGTH: 129
<212> TYPE: DNA
<213> ORGANISM: Artificial Sequence
<220> FEATURE:
<223> OTHER INFORMATION: Description of Artificial Sequence: Synthetic
      DNA/RNA sequence
<220> FEATURE:
<223> OTHER INFORMATION: Description of Combined DNA/RNA Molecule:
      Synthetic DNA/RNA sequence

<400> SEQUENCE: 7
catgctgtca gtaccaccat cacaggttgg tctggtctcu uaccaccttc tcacggctca    60
acgttcctat tcggtttttt tgcaaatgtt atcgaggtcc ggcgagacca gaccaacctg   120
tgattttttt                                                         129

<210> SEQ ID NO 8
<211> LENGTH: 129
<212> TYPE: DNA
<213> ORGANISM: Artificial Sequence
<220> FEATURE:
<223> OTHER INFORMATION: Description of Artificial Sequence: Synthetic
      DNA/RNA sequence
<220> FEATURE:
<223> OTHER INFORMATION: Description of Combined DNA/RNA Molecule:
      Synthetic DNA/RNA sequence

<400> SEQUENCE: 8
catgctgtca gtaccaccat cacaggttgg tctggtctct taccaccuuc tcacggctca    60
acgttcctat tcggtttttt tgcaaatgtt atcgaggtcc ggcgagacca gaccaacctg   120
tgattttttt                                                         129

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic -continued

```
        oligonucleotide

<400> SEQUENCE: 9
gagaccagac caacctgtga                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 10
tcacaggttg gtctggtctc                                              20
```

MULTIPLEX PCR

CROSS-REFERENCE TO RELATED APPLICATIONS

This application claims priority from U.S. Provisional Application Ser. No. 60/331,693, filed Nov. 19, 2001, the disclosure of which is incorporated herein by reference in its entirety.

BACKGROUND OF THE INVENTION

Amplification of nucleic acids and analysis of the resulting amplification products has revolutionized the basic and clinical sciences. Applications of these techniques include molecular cloning, nucleic acid sequencing, genotyping, detection and identification of single nucleotide polymorphisms (SNP) and other polymorphisms and mutations and the quantitation of gene expression, Various techniques for nucleic acid amplification have been developed, such as strand displacement amplification, transcription-based amplification, and polymerase chain reaction (PCR).

Use of PCR in large scale research projects and in clinical applications entails amplification of many distinct target sequences with the concomitant generation of a great number of PCR amplicons. As the scale of such projects increases, it has become cost prohibitive and inefficient to undertake the necessary reactions singly. Thus, there is great interest in developing methods of performing multiple amplification reactions in parallel in the same reaction vessel using a common pool of template and reagents.

Such multiplex PCR methods, in which multiple pairs of target-specific primers are used to coamplify multiple targets, have met with only qualified success. Combining all the required primers in the same tube greatly increases the frequency of formation of primer-dimer and other spurious amplification products. As the number of primer pairs rises in multiplex PCR, the number of potential primer-dimer interactions (or spurious amplicons generated by two different primers) increases exponentially according to the number of primers used.

Even with careful attention paid to the design of the multiplex primer pairs to avoid obvious primer-dimer incompatibilities, conventional multiplex PCR is generally limited to about 10-20 simultaneous amplification reactions before undesired amplification products predominate.

Different approaches to ameliorate the problems associated with multiplex PCR have been developed, but none with unqualified success.

PCT publication WO 96/41012 discloses a method for multiplex PCR that entails two rounds of amplification and that uses primer pairs comprising template-specific sequences at their respective 3' ends and universal, or common, primer sequences at their respective 5' ends. The first round of amplification uses the specific primer sequences and the second amplification uses the universal primer sequences. The second round normalizes differential binding of the specific primers to different templates.

Another multiplex method uses a single specific primer for each target and a single common primer. N. E. Broude, et al., Multiplex allele-specific target amplification based on PCR suppression, Proc. Natl. Acad. Sci. USA 98:206-211 (2001). This method still suffers from the amplification of spurious products, however, and therefore remains limited in its application.

Thus, there remains a need in the art for methods of simultaneous multiplex amplification of large numbers of specific nucleic acid sequences that minimizes coamplification of spurious reaction products.

SUMMARY OF THE INVENTION

It is, therefore, an object of the present invention to provide novel and improved methods that substantially reduce the formation of spurious reaction products in multiplex amplification reactions of large numbers of specific nucleic acid sequences.

It is further an object of the present invention to provide novel compositions useful in substantially reducing the formation of spurious reaction products in multiplex amplification reactions of large numbers of specific nucleic acid sequences.

The present invention is based, in part, on the novel use of two rounds of specific hybridization between a homology region in a probe and the complementary sequence in a nucleic acid template, each of which is followed by extension of the probe by DNA synthesis.

Accordingly, in a first aspect, the present invention provides for a method of nucleic acid amplification by which a linear amplification molecule contacts a nucleic acid template under conditions that support its specific hybridization thereto. In some embodiments, the linear amplification molecule is a DNA oligonucleotide. According to some embodiments the template is DNA and in other embodiments template is RNA.

In the next step, one or more nucleotides complementary to corresponding nucleotides present in the template are added sequentially to the linear amplification molecule at the end hybridized to the template, resulting in the formation of an extended linear amplification molecule. In some embodiments, addition of complementary nucleotides is carried out using a DNA polymerase.

In the next step, the extended linear amplification molecule is incubated under conditions that support its specific intramolecular hybridization, resulting in the formation of a double-stranded intramolecular hybridization region in which one of the strands includes nucleotides newly added in the prior step.

In the next step, the extended linear amplification molecule is cleaved at a predetermined site, resulting in the formation of a first and a second fragment that remain non-covalently bound to each other along the intramolecular hybridization region. In some embodiments, cleavage occurs using an enzyme that cleaves at an apurinic site formed in the linear amplification molecule. In other embodiments, cleavage is effected using a chemical agent.

In the next step, to the end newly created by the cleavage, one or more nucleotides complementary to corresponding nucleotides present in the second fragment are added sequentially to the first fragment, resulting in the formation of an extended first fragment. In some embodiments, addition of complementary nucleotides is carried out using a DNA polymerase that uses the first fragment as primer and the second fragment as template.

In an optional last step, the extended first fragment is used as template in an exponential amplification reaction, such as PCR. Where multiple amplifications are desired to be carried out in parallel in the same reaction, common primers can be used in the PCR.

After PCR, the exponentially amplified sequences from the starting template is analyzed.

In another aspect, the present invention provides for an alternative method of nucleic acid amplification in which no cleavage occurs. In the first step, a linear amplification molecule contacts a nucleic acid template under conditions that support its specific hybridization thereto. In the next step, one or more nucleotides complementary to corresponding nucleotides present in the template are added sequentially to the linear amplification molecule at the end hybridized to the template, resulting in the formation of an extended linear amplification molecule. In the next step, the extended linear amplification molecule is incubated under conditions that support its specific intramolecular hybridization, resulting in the formation of a double-stranded intramolecular hybridization region in which one of the strands includes nucleotides newly added in the prior step. In the next step, nucleotides added in the first extension step but that are not included in the double-stranded intramolecular hybridization region, i.e., which are single-stranded, are removed from the end of the extended linear amplification molecule. In the next step, at the end hybridized in the double-stranded intramolecular hybridization region, one or more nucleotides are added sequentially to the extended linear amplification molecule which are complementary to nucleotides present in the linear amplification molecule, thereby fully extending the linear amplification molecule. In an optional last step, the fully extended linear amplification molecule is used as a template in an exponential amplification reaction, such as PCR.

According to alternative embodiments, the present invention provides additional methods useful for further reducing the formation of spurious reaction products. Thus, one embodiment provides for the elimination of linear amplification molecules that fail to hybridize to template. In other embodiments, one or more uracil bases is included in the linear amplification molecule and the first probe extension by DNA synthesis is carried out using a DNA polymerase that stalls upon encountering a uracil base in a template. In yet other embodiments, biotinylated nucleotides are either incorporated into the linear amplification molecule or used during the second probe extension by DNA synthesis. Thereafter, a streptavidin coated substrate is used to purify biotinylated complexes away from molecules that contribute to formation of spurious reaction products.

According to yet another aspect, the present invention also provides a linear molecule for nucleic acid amplification. The linear molecule includes a first primer region substantially similar to a first primer sequence, a first homology region substantially similar to the sequence of a first region of a nucleic acid, a cleavable site, a second primer region substantially similar to a second primer sequence, and a second homology region substantially similar to the complement of the sequence of a second region of the nucleic acid, wherein the first and second homology regions of the nucleic acid are present on the same strand of the nucleic acid, and wherein the first nucleic acid homology region is closer to the 5' end of the strand than the second nucleic acid homology region. Usefully, according to some embodiments, the linear amplification molecule is a DNA oligonucleotide.

According to alternative embodiments, the present invention provides linear amplification molecules further comprising a barcode sequence, i.e., a unique pattern of nucleotides that uniquely identifies the linear amplification molecule with which it is associated; further comprising a fluorescent dye label; further comprising an affinity capture label, such as biotin; and further comprising a uracil base. According to yet other embodiments, the cleavage site of the linear amplification molecule is capable of being cleaved by an enzyme or chemical agent, or is capable of forming an apurinic site.

In another aspect, the present invention provides for an alternative linear molecule for nucleic acid amplification containing one primer sequence and no cleavage site. According to this embodiment, the linear amplification molecule includes a first primer region substantially similar to a first primer sequence, a first homology region substantially similar to the sequence of a first region of a nucleic acid, and a second homology region substantially similar to the complement of the sequence of a second region of the nucleic acid, wherein the first and second homology regions of the nucleic acid are present on the same strand of the nucleic acid, and wherein the first nucleic acid homology region is closer to the 5' end of the strand than the second nucleic acid homology region.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which:

FIG. 2A further illustrates optional method steps for eliminating unhybridized loopback probes and reducing the incidence of spurious amplification products. The order of steps is not necessarily limiting.

FIG. 2B illustrates additional optional method steps for further reducing the incidence of spurious amplification products. The order of steps is not necessarily limiting.

FIG. 8A illustrates the structure of a probe capable of supporting self-priming and sustained amplification, as well as the first four steps of a method using the probe for nucleic acid amplification, according to the present invention.

FIG. 8C illustrates four further steps of the method using the probe of FIG. 8A for nucleic acid amplification.

DETAILED DESCRIPTION OF THE INVENTION

Figure 1A:
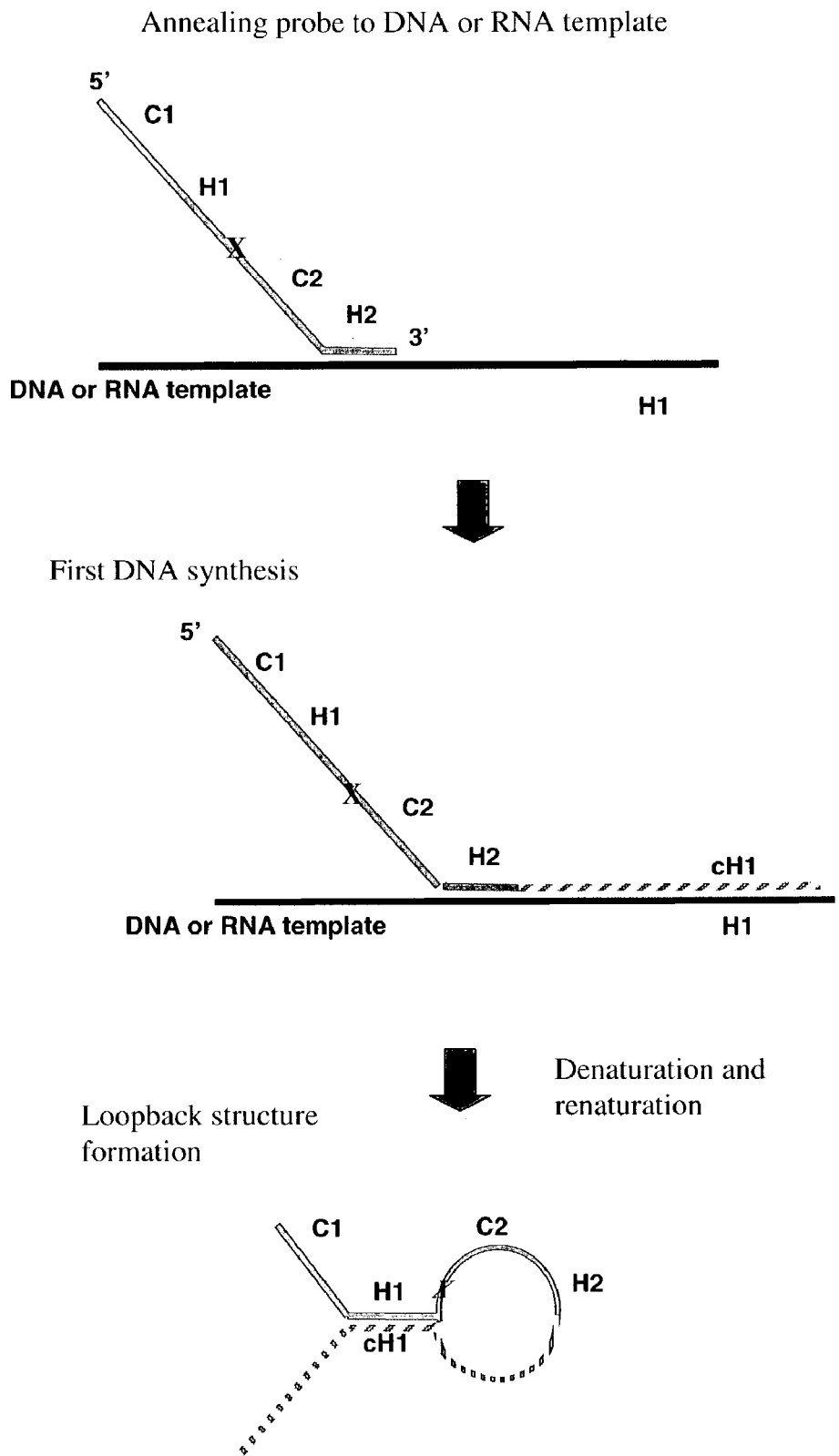
FIG. 1A schematizes the structure of a first embodiment of a loopback probe of the present invention and the first three steps of a first embodiment of a method of the present invention for nucleic acid amplification, including probe-template hybridization, probe extension and extended probe intramolecular hybridization.

The compositions and methods disclosed herein advantageously improve the performance of nucleic acid amplification, particularly multiplexed amplification methods in which multiple templates are amplified in parallel in the same reaction using many different primer pairs. As understood by those of ordinary skill in the art, conventional multiplex amplification methods are prone to the generation of spurious amplification products that can hinder amplification or analysis of desired, specific amplicons.

As discussed in further detail below, the compositions and methods of the instant invention are used to obtain from a first template a complementary second template having common primer sequences which can then be amplified exponentially for subsequent analysis. Obtaining the second template from the first template is effected by two rounds of specific hybridization coupled with extension of the linear amplification molecule by DNA synthesis, which has the effect of substantially reducing the formation and amplification of spurious reaction products. Use of such extensions by DNA synthesis also permits the use in reactions of much lower amounts of the sequence-specific reagents of the instant invention, which results in a substantial cost savings and also further contributes to reducing the formation and amplification of spurious products.

Multiple sequences in the first template, e.g., genomic DNA, can be converted in parallel to distinct second template molecules containing complementary sequences. Because each sequence present in the second template molecules is flanked by common primer sequences, it is thereafter possible to simultaneously amplify all the sequences present in the second templates by PCR using a single pair of common primers. In contrast to conventional multiplex PCR, this further drastically reduces the opportunity for spurious reaction products to be generated and amplified.

A first embodiment of the compositions of the present invention usefully provides a linear amplification molecule (herein synonymously called a "probe," a "loopback probe," a "linear amplification molecule" or a "linear molecule") to be used in the methods of amplification which are further described herein. As used herein, "linear" refers a molecule formed of an unbranched polymer, e.g., DNA or RNA. Presence of secondary or tertiary structure does not render a probe not linear.

Probes are designed to specifically hybridize to a template nucleic acid, to be subsequently amplified. Template can be DNA or RNA. If RNA, the RNA template can also be converted to DNA using methods well known to the skilled artisan. Template can be obtained from a variety of sources, including but not limited to viruses, bacterial cells, fungal cells, plant cells, animal cells, mammalian cells and human cells. Template nucleic acid can also take the form of genomic DNA or RNA, or episomal DNA or RNA.

If the template is double stranded, a particular probe is designed, as discussed below, to specifically hybridize to only one of the two possible strands comprising the double stranded template.

Typically, probes are single stranded oligonucleotides and may be made of DNA exclusively, RNA exclusively or combinations of RNA and DNA, RNA and protein, DNA and protein or RNA and DNA and protein. Probes can also be modified with a wide array of modified bases or chemical substituents. For example, probes can be labeled with a fluorescent dye molecule to facilitate analysis of reactions in which probes participate. Probes can also be labeled with biotin, or other affinity capture moieties, according to the need of the skilled artisan. Methods of synthesizing oligonucleotide probes and modified oligonucleotides are well within the knowledge of those of ordinary skill in the art.

Oligonucleotide probes useful in the present invention can be of various lengths, including as long as about 40 nucleotides (nt), 50 nt, 60 nt, 70 nt, 80 nt, 90 nt, 100 nt, 150 nt, 200 nt, 250 nt, 300 nt, 400 nt, 500 nt, 600 nt, 700 nt, 800 nt, 900 nt, 1000 nt or longer. Oligonucleotide probes can also be as short as about 950 nt, 850 nt, 750 nt, 650 nt, 550 nt, 450 nt, 350 nt, 275 nt, 225 nt, 175 nt, 125 nt, 95 nt, 85 nt, 75 nt, 65 nt, 55 nt, 45 nt, 35 nt or shorter.

The generic structure of the loopback probes of the instant invention comprises multiple regions, each of which confers a particular function. The generic structure is schematized in the top panel of FIG. 1A.

At the 5' end of the probe lies a first common primer sequence, called "C1." C1 may begin immediately with the 5' most nucleotide of the probe, or may be inset toward the 3' end of the probe by one or more nucleotides. The sequence of C1 is identical or substantially the same as the sequence of a first PCR primer, further discussed herein.

After C1 (moving toward the 3' end of the probe) is a first homology sequence called "H1." H1 is identical or substantially similar to a sequence found in the template nucleic acid to be amplified using the methods disclosed herein. Zero, or one or more nucleotides can separate C1 from H1. C1 and H1 may even overlap by one or more nucleotides.

After H1 is a second common primer sequence called "C2." The sequence of C2 is identical or substantially similar to the sequence of a second PCR primer, further discussed herein, which is typically distinct in sequence from C1. Zero, or one or more nucleotides can separate C2 from H1. C2 and H1 may even overlap by one or more nucleotides.

Between H1 and C2 is a cleavable site shown as "X" in FIG. 1 and elsewhere. X is a sequence of nucleotides or a natural or non-natural chemical structure present in the probe that is specifically recognized and cleaved by a cleaving agent. Cleavage is associated with the breaking of one or more covalent bonds responsible for holding together the probe as a discrete molecular entity. Such bonds may be present in the sugar-phosphate backbone of the probe, or in a non-natural cleavable chemical linkage. After cleavage, H1 and C2 are no longer physically connected.

Cleavage affects only one strand. Thus, if part of the probe forms a double strand with another sequence then cleavage cuts the probe strand but not the strand with which the probe is paired. However, the cleavage site recognized by the cleaving agent may be present in the probe alone, or in a double strand structure formed between the probe and another sequence. As will be discussed further herein, such other sequence can be present in an enzymatic extension product of the probe.

Many types of cleavage sites and corresponding cleaving agents are known to those of ordinary skill in the art. The following examples are not to be considered limiting.

Cleavage sites include a specific pattern of nucleotides recognized by an endonuclease that recognizes double-stranded DNA but is capable only of cutting single-stranded DNA (i.e., the probe strand). Examples of such endonucleases include N.AlwI, N.BstNBI, N.BbvCIA and N.BbvCIB (all of which are sold by New England Biolabs, Inc. (Beverly, Mass., USA)).

A ribose sugar can be incorporated into a desired position in the deoxyribose sugar-phosphate backbone of a probe. Thereafter, a ribonuclease can be used to cleave the ribose-phosphate bond leaving a 3' hydroxyl group.

A uracil base can be incorporated at a desired position in the probe. Thereafter, the uracil base can be removed by treating the probe with the enzyme uracil-DNA glycosylase (UDG) to generate an apurinic (AP) site. The AP-site then can be cleaved chemically or with enzymes such as AP-endonucleases or AP-lyases.

A "damaged" base can be incorporated at a desired location in the probe. Thereafter, the damaged base can be removed by treating the probe with a glycosylase to generate an AP-site which can then be cleaved chemically or with enzymes such as AP-endonucleases or AP-lyases.

Examples of damaged bases include urea, 5,6-dihydroxythymine, thymine glycol, 5-hydroxy-5-methylhydantoin, uracil glycol, 6-hydroxy-5,6-dihydrothymine, methyltartronylurea, 8-oxoguanine, 8-oxoadenine, fapy-guanine, methyl-fapy-guanine, fapy-adenine, aflatoxin B1-fapy-guanine, 5-hydroxy-cytosine, and 5-hydroxy-uracil.

Examples of enzymes that combine glycosylase and AP-lyase activities include endonuclease III (Nth), Fpg and hOGG1 (all sold by New England Biolabs, Inc.).

Cleavage sites may also be cleaved by chemical agents that recognize and cleave specific chemical linkages present in the probe.

The cleavable site X can be present in or 3' of H1 but typically does not overlap C2. It follows then that depending on the position of X, cleavage can occur in H1, immediately after H1 (i.e., leaving H1 flush with the 3' end of the cleaved probe) or some distance 3' of H1.

After C2 is a second homology sequence called "H2," distinct in sequence from H1. H2 is perfectly or substantially complementary to a corresponding sequence present in the template nucleic acid, called "cH2," meaning "complementary to H2." Thus, under appropriate conditions, H2 and cH2 can hybridize with each other by classic Watson-Crick type hydrogen bonds. This is in contrast to H1, which is found both in probe and template. Thus, H1 of probe does not typically hybridize to H1 of template. In the probe, H1 is 5' to H2, whereas in the template, H1 is 5' to cH2.

Typically, H2 terminates at the 3' end of the probe, such that the 3'-most nucleotide of the probe specifically pairs with the 5'-most nucleotide of cH2. Zero or one or more nucleotides can separate C2 from H2. C2 and H2 may even overlap by one or more nucleotides.

Because C1 and C2 are used in PCR primers, their length and sequence are chosen to maximize the specificity and efficiency of PCR and to minimize the synthesis of incorrect PCR products. Methods of designing such sequences are well known to those of skill in the art and can be accomplished empirically or theoretically using computerized algorithms.

The length of C1 or C2 may be as long as about 15 nt, 25 nt, 35 nt, 45 nt, 55 nt, 65 nt, 75 nt, 85 nt, 95 nt, 105 nt or longer. The length of C1 or C2 may also be short as about 100 nt, 90 nt, 80 nt, 70 nt, 60 nt, 50 nt, 40 nt, 30 nt, 20 nt, 10 nt or shorter. Typically, the length of the C1 or C2 is between about 15 to about 40 nucleotides.

The choice of the sequence of H1 and H2 is primarily dictated by the region of template desired to be amplified and the desired size of the amplicon. For example, if the skilled artisan wishes to interrogate a region of a gene for the presence of SNP variants, the sequences of H1 and H2 flank the location of the SNP in the gene. If multiple sites in the same gene harboring SNPs are to be interrogated, then H1 and H2 can be chosen to flank a longer template sequence.

The length of H1 and H2 can be varied according to the needs of the skilled artisan, but the minimum length of H2 is dictated by the complexity of the population of nucleic acids present in the sample containing the template. Other variables held constant, the greater the complexity of the population, the longer H2 should be to uniquely recognize and hybridize to a complementary cH2 sequence present in the template.

The length of H1 or H2 may be as long as about 15 nt, 25 nt, 35 nt, 45 nt, 55 nt, 65 nt, 75 nt, 85 nt, 95 nt, 105 nt or longer. The length of H1 or H2 may also be short as about 100 nt, 90 nt, 80 nt, 70 nt, 60 nt, 50 nt, 40 nt, 30 nt, 20 nt, 10 nt or shorter. Typically, the length of the H1 or H2 is between about 15 to about 40 nucleotides.

The number of nucleotides separating H1 and cH2 in the template can vary greatly. H1 and cH2 can be close together or the distance separating them reach several kilobases or more. As will become apparent below, the only limitations on the distance between H1 and cH2 in the template is the processivity of the DNA polymerases used to extend the cleaved probe and amplify the extension product. The distance separating H1 and cH2 in the template does not necessarily correspond to the distance separating H1 and H2 in the probe.

The sequence of probe H2 need not be perfectly complementary to the sequence of cH2 present in the template and the sequence of probe H1 need not be identical to the sequence of H1 of the template. Rather sequence differences are permissible as long as sufficient specificity of hybridization is retained.

Sequence differences between probe and template homology regions can be expressed in degrees of homology or sequence relatedness. Thus, one can compare the probe H2 sequence with the complement of the template cH2 sequence to determine their degree of homology and one can do likewise as between the probe H1 sequence and the sequence of H1 present in the template.

Homology between such sequences can be calculated using computerized algorithms. For purposes herein, percent identity or complementarity (homology) is calculated using the procedure of Tatiana et al., *FEMS Mirobiol. Lett.* 174:247-250 (1999), which procedure is effectuated by the computer program BLAST 2 SEQUENCES, available online at the National Center for Biotechnology Information (NCBI) website.

The extent of homology between probe and template homology regions that is deemed sufficient is within the discretion of the skilled artisan. For example, if the template is present in a complex mixture of nucleic acids, e.g., genomic DNA, a high degree of homology is typically used, such that the probe hybridizes with sufficient specificity to the intended region of the template. If the homology is insufficiently high and/or the region of homology is insufficiently long, probe will hybridize incorrectly to one or more non-specific templates, yielding uninformative amplification products, i.e., spurious products or background products. Where template is present in a less complex mixture of nucleic acids, a lesser degree of homology and/or a shorter region of homology may be acceptable. The degree of homology that is acceptable can be determined by the skilled artisan empirically or theoretically.

As understood by the skilled artisan, factors in addition to the overall length of the hybridization region and percentage homology can affect specificity of hybridization, including temperature and salt concentrations, are also relevant. Chemical additives, such as cetyltrimethylammonium bromide (CTAB) can also affect hybridization specificity of RNA:DNA duplexes, as further described in WO 02/29112, the disclosure of which is herein incorporated by reference in its entirety.

The percent homology between probe region H2 and template region cH2 and the degree of homology between probe region H1 and template region H1 may usefully be as high as about 60%, 70%, 80%, 82%, 84%, 86%, 88%, 90%, 92%, 94%, 96%, 98% or 100%. The percent homology may also usefully be as low as about 99%, 97%, 95%, 93%, 91%, 89%, 87%, 85%, 83%, 81%, 75%, 65% or 55%.

For purposes of the present invention, a first sequence is considered to be "substantially similar" to a second sequence if the sequences possess the requisite level of homology as determined by the skilled artisan. Thus, if under particular conditions, the extent of homology is sufficiently high to support specific hybridization between the first sequence and the complement of the second sequence, or between the second sequence and the complement of the first sequence, then the sequences are considered to be substantially similar to each other.

The present invention also usefully provides methods of amplifying template nucleic acid using a loopback probe.

A first embodiment of such a method is described with reference to FIG. 1. According to this embodiment, the probe is first contacted to the template under appropriate conditions to effect specific hybridization between the probe H2 region and the cH2 region of the template to form a double-stranded duplex structure (FIG. 1A).

Typically, an aqueous solution containing probe and template, as well as other constituents such as salts and buffers, is prepared and heated to denature the template. The mixture is then allowed to cool, either naturally or at a controlled rate, such that hybridization between H2 and cH2 is effected.

Techniques for determining conditions that will support specific hybridization between H2 and cH2 are well known to those of ordinary skill in the art. Variables that can be altered to affect the specificity and speed of hybridization include but are not limited to concentration of probe, concentration of template, concentration of monovalent cations (e.g., sodium or potassium) and other ions, temperature, concentration of polyamines (e.g., spermine or spermidine), pH and concentration of buffer components.

In a second step, schematized in the middle panel of FIG. 1A, the probe is extended from its 3' end using a DNA polymerase that reads the template in synthesizing the extended probe. If it is desired to extend only those probes that are perfectly matched to the template at their 3' end, use of a DNA polymerase lacking a 3'-to-5' single-stranded exonuclease correcting activity is preferred. In this manner, it is possible to selectively extend only those probes that are hybridized at a threshold level of specificity to template.

If the template is RNA, then the DNA polymerase is advantageously a reverse transcriptase (RT), including reverse transcriptase lacking 3'-to-5' exonuclease activity (e.g., AMV-RT).

Upon reaching the H1 sequence present in the template, the polymerase will synthesize as part of the extended probe a sequence complementary to H1 called cH1. In the case of DNA template, probe extension continues until the polymerase falls off the template or until the reaction is stopped. In the case of mRNA template, probe extension typically continues until the RT encounters the end of the transcript.

After probe extension is complete, the mixture of extended probe and template is heated to melt apart the probe and template. The mixture is then cooled to allow the extended probe to hybridize intramolecularly (also called unimolecular hybridization). At a low enough temperature the H1 region (present in the original probe) and cH1 (present in the extended part of the probe) encounter each other and specifically hybridize to form a stable double-stranded duplex (also called an intramolecular hybridization region), thereby yielding the stem-loop structure ("loopback structure") pictured in the lower panel of FIG. 1A.

Hybridization should be effected at a temperature low enough to support hybridization between H1 and cH1, i.e., not exceed the melting temperature of the hybrid, but should also be high enough to suppress adventitious non-specific hybridization. Hybridization can be carried out at temperatures as high as 30° C., 40° C., 50° C., 60° C., 70° C., 80° C., 90° C., 100° C. or higher. Hybridization can also be carried out at temperatures as low as 95° C., 85° C., 75° C., 65° C., 55° C., 45° C., 35° C., 25° C. or lower. Usefully, hybridization is carried out at a temperature of at least 50° C.

While not wishing to be bound by theory, it is believed that when H1 and cH1 are present in the same molecule (e.g., extended probe), their effective concentration is very high as compared to the actual concentration of extended probe molecules and template and is a function of the distance separating them. For example, if H1 and cH1 are within approximately 100 nt of each other, their effective local concentration is in the millimolar range; as the distance increases, the effective concentration decreases. Preferably, the spacing between the 3' end of H1 and the 5' end of cH1 is several hundred nucleotides.

If intermolecular hybridization is expected to be insufficiently favored, e.g. because the concentration of template is high, conditions can be modified to favor unimolecular over bimolecular interactions. For example, the salt concentration can be reduced or the mixture can be diluted.

Figure 1B:
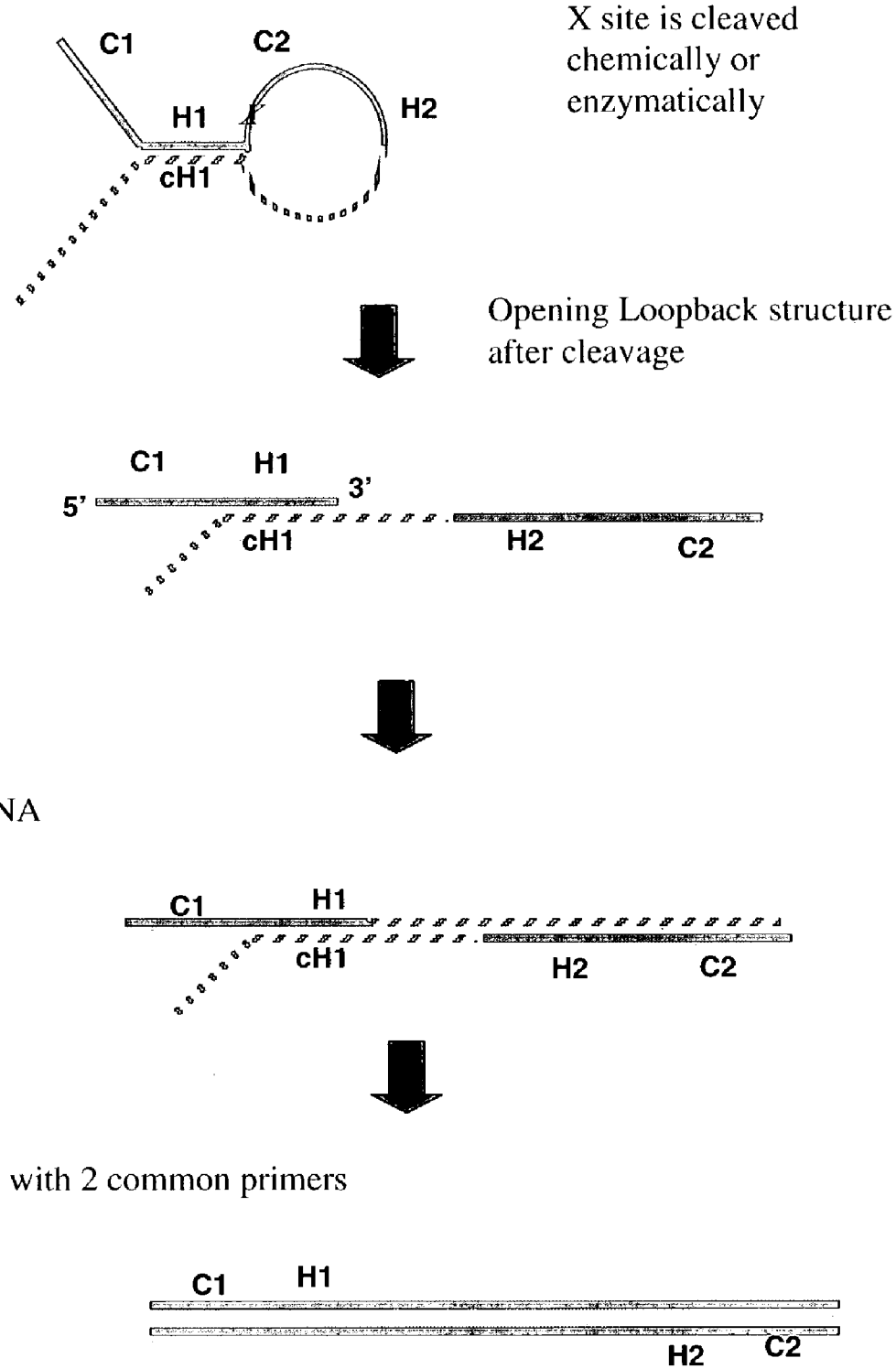
FIG. 1B illustrates an additional three steps of a method of nucleic acid amplification according to the present invention, including cleavage of the self-hybridized probe, extension and exponential amplification by PCR.

In a fourth step, illustrated in the top panel of FIG. 1B, the loopback structure is cleaved at the cleavable site X between H1 and C2. Conditions for cleavage should be chosen to preserve the duplex structure formed by the H1-cH1 hybrid, e.g., cleavage should be effected at a temperature below the melting temperature of the duplex. Regardless of how cleavage is effected, it desirably should leave a 3' hydroxyl group to which nucleotides can be added by action of a polymerase. Alternatively, if cleavage does not yield a 3' hydroxyl group, the cleavage product may be treated in a manner according to the knowledge of the skilled artisan to generate an end to which a polymerase can specifically add nucleotides.

Cleavage desirably occurs flush with the end of H1, thereby leaving no 3' overhang, but can also occur within H1 (i.e., in the duplex region) or in the single-stranded region (if present) between H1 and C2 (thereby leaving a 3' overhang). Regardless where cleavage occurs, it should leave C2 intact. If cleavage occurs in the double-stranded duplex, cleavage should only cleave the single strand of the duplex containing H1 and should not cleave the single strand containing cH1, i.e., the extended probe region containing cH1 should remain intact.

Cleavage converts the extended loopback probe, formerly a single molecule, into two fragments. Under appropriate conditions, the fragments remain noncovalently bound to each other in the double-stranded region formed by the specific hybridization between H1 and cH1.

After cleavage, the loop between H1 and cH1 opens. As illustrated in the second panel of FIG. 1B, the "top strand" (first fragment) now comprises (5' to 3') C1 and H1, whereas the "bottom stand" (second fragment) now comprises (5' to 3') C2, H2 and cH1. Absent nonspecific interactions, only the duplex formed between H1 on the top stand and cH1 on the bottom stand hold the now physically distinct strands together.

The fifth step, schematized in the third panel from the top in FIG. 1B, is a second round of extension using a DNA polymerase, which may be carried out under similar conditions as in the first round, discussed above.

If cleavage left no 3' unpaired nucleotides after H1, then extension can be effected using a DNA polymerase lacking proofreading activity, if desired. In this second extension step, the DNA polymerase uses H1 alone as a primer, reading the bottom strand and adding nucleotides to the 3' end of H1. Extension stops when the polymerase reaches the end of the bottom strand, after C2. The extension product contains the complement of H2 as well as the complement of C2 (cC2). The fully extended top strand comprises (5' to 3') C1, H1, cH2 and cC2 and contains all the information necessary for it to serve as a second template, distinct from the first template discussed above, in a subsequent polymerase chain reaction.

If cleavage did leave 3' unpaired nucleotides after H1 then it is necessary to remove them before polymerization can occur. This can be accomplished by first treating the cleaved extended probe with a 3'-to-5' single-stranded exonuclease. Alternatively, it is possible to use a DNA polymerase containing a 3'-to-5' exonuclease proofreading activity. In either case, all 3' unpaired nucleotides will be removed, including those present on the bottom strand, i.e., after cH1. If this occurs, extension by the DNA polymerase will also occur on the bottom strand using sequences 5' of H1 as template. This will yield a fully extended bottom strand comprising (5' to 3') C2, H2, cH1 and cC1.

In a later, sixth step, the extended top and/or bottom stand, as illustrated in the bottom panel of FIG. 1B, is used as template in an exponential amplification reaction, such as PCR.

For PCR, common primers C1 and C2 are added to a reaction mixture containing the extended top and/or bottom strands as a template. During the first cycle of PCR, common primer C2 hybridizes to the complementary sequence cC2 at the 3' end of the extended top strand. C2 then serves as primer for extension by a DNA polymerase to form extended bottom stand, which contains (5' to 3') C2, H2, cH1 and cC1. By virtue of the presence of the cC1 sequence, the extended bottom strand can then serve as template for extension of common primer C1 in the second round of PCR.

If extended bottom strand was generated during the fifth step, then in the first round of PCR common primer C1 can prime off of the bottom strand as template to yield a new top strand.

Subsequent cycles then give rise to exponentially amplified product. All the conditions and components necessary for PCR are within the knowledge of the skilled artisan.

It is important to note that because the original probe, the extended probe and the cleaved extended probe each contain C1 and C2, and not the complementary sequence of C1 or C2 (i.e., cC1 and cC2), none of these molecules can serve as template for PCR using C1 or C2 as primers. Generation of spurious PCR products is therefore advantageously minimized. As a result, in some embodiments of the present invention, it is possible for common primers C1 and C2 to have been present during all the steps of the method disclosed above. Their competence to serve as specific primers is completely dependent upon the presence of an extended top or bottom strand formed in the fifth step of the method.

The amplified sequence (amplicon) can then be further analyzed according to the knowledge of the skilled artisan. For example, the sequence flanked by H1 and H2 can be sequenced to identify SNP variants.

Use of the method disclosed above, in addition to alternative embodiments thereof, to amplify nucleic acid sequences of interest offers significant advantages over other methods of amplification, particularly in the context of multiplex amplification.

In conventional PCR a pair of PCR primers, analogous to H1 and H2, is used to amplify the template. Because of the exponential nature of PCR, this can give rise to spurious PCR products due to formation of primer-dimers and non-specific hybridization of primers to template. In fact, in some reactions, spurious products predominate over specifically amplified products, especially where the template is very complex, e.g., genomic DNA.

The compositions and methods of the present invention advantageously avoid these problems in a number of ways. First, the two specific hybridization events of the present invention are serial and not parallel, as in conventional PCR. That is, in conventional PCR both primers (again, analogous to H1 and H2) are competent to hybridize to template and be extended. As a result, exponential amplification begins from the first cycle of PCR, often giving rise to spurious products. In the methods of the present invention, however, only a single hybridization event occurs in the first step, i.e., H2 hybridizes to template, which is followed by a single round of extension of the probe by DNA synthesis, i.e., extension of the probe using the H2 sequence as primer. If H2 hybridizes to the wrong sequence, then even if extension occurs, it is unlikely that H1 will non-specifically hybridize intramolecularly with the extended probe sequence. If any other part of the probe sequence incorrectly hybridizes to template (including H1, for example), then no extension could occur because the 3' end of the probe would be free (unlike when H2 hybridizes correctly to its complement). In contrast, if H1 were not part of the same molecule as H2, there is a far greater likelihood that it could successfully misprime.

After the first hybridization and probe extension step, the subsequent hybridization and probe extension step is only likely to be successful if the extended probe contains the correct complementary sequence for H1 (i.e., cH1). Further, only if the second hybridization and extension step is successful can exponential amplification using the common primers C1 and C2 be successful.

Thus each step in the methods of the present invention operates to inhibit the formation of spurious extension products, which is especially advantageous in the context of multiplex PCR. In conventional multiplex PCR, many separate primer pairs are used simultaneously in the same reaction. Such simultaneous use can significantly exacerbate the formation of spurious PCR products because there is much greater opportunity for primers to interact with each other and to hybridize non-specifically to the template and thereby misprime. In multiplex PCR using the compositions and methods of the present invention, however, half as many probes are used and the limitations discussed above dramatically suppress formation of spurious PCR products during the exponential amplification phase.

An additional advantage in the context of multiplex amplification is that a single set of common primers, i.e., C1 and C2, can be used to exponentially amplify multiple amplicons. As a result, under one set of reaction conditions all the amplicons are expected to be amplified with equivalent efficiency (disregarding issues of amplicon length and secondary structure). It is therefore expected that amplicons will be stoichiometrically represented in the final reaction product, whereas in conventional multiplex PCR, some inefficiently amplified amplicons can be "crowded out" by amplicons amplified more efficiently, resulting in their effective absence from the final reaction product. Thus, it is not necessary for the skilled artisan to empirically determine a set of reaction conditions that will be effective at amplifying multiple amplicons, wherein each amplicon is exponentially amplified using a separate pair of primers. This saves significant amounts of time and materials costs, and increases the likelihood that all amplicons of interest will be present in the final reaction product.

Although the foregoing discussion has focused on multiplex amplification of a plurality of nucleic acid sequences of interest, the present invention can also advantageously be applied to amplifications of a single sequence of interest.

As discussed above, a significant advantage of the compositions and methods of the present invention is that the common primers used for amplification cannot specifically hybridize to and prime off the loopback probes or other products of the loopback probes. This results in a lower incidence of spurious amplification products. According to other embodiments of the present invention, however, it is possible to yet further reduce this background. Such additional embodiments may be practiced singly or in combination to maximize suppression of background.

Figure 2A:
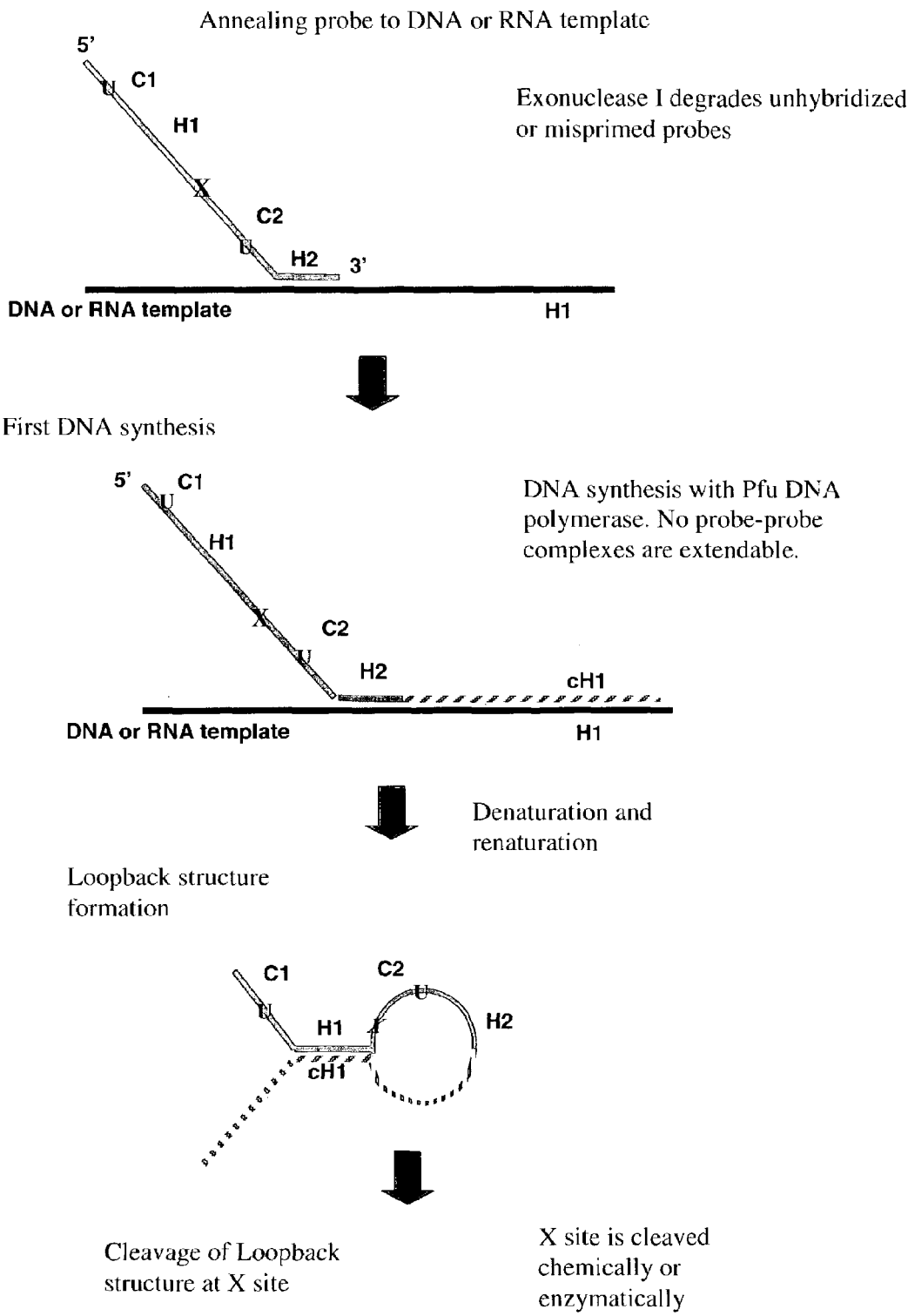
FIG. 2A illustrates an alternative embodiment of the loopback probe of the present invention in which uracil bases are present in the common primer sequences.

Thus, according to an alternative embodiment of the methods disclosed herein illustrated in FIG. 2A, it is possible, after the step of hybridizing the loopback probes to template, to treat the mixture with a 3'-5' single-stranded exonuclease, e.g., Exonuclease I (ExoI). Such treatment can beneficially reduce the number of incorrectly hybridized and unhybridized probe molecules, and thereby reduce the incidence of spurious product synthesis. For example, where loopback probes have hybridized nonspecifically to template, have formed probe primer-dimers or have hybridized intramolecularly to leave one or more unpaired 3' nucleotide, treatment with an exonuclease can degrade the misprimed probes.

According to another alternative, it is possible to capture only those probes that have hybridized to the template and to purify the probe-template combination away from unhybridized probe. As an example of this approach, an affinity capture moiety, e.g., biotin, can be incorporated into the DNA or RNA template using techniques well known to those of ordinary skill in the art. For example, free 3' ends of DNA can be generated by physically shearing DNA or by digestion with a restriction endonuclease after which biotinylated nucleotides are added using a terminal transferase enzyme.

After incorporation of the affinity capture moiety, loopback probes are hybridized to the template, after which the mixture is incubated with beads or another substrate coated with the other component of the affinity-capture system which is capable of specifically binding the affinity capture moiety. For example, if the affinity capture moiety is biotin, the other component of the affinity capture system is streptavidin or other biotin-binding moiety. The beads, having captured the template, are then washed to remove unhybridized probe, followed by elution of the probe-template combinations for use in subsequent steps of the disclosed methods.

According to another embodiment, it is also possible to suppress probe primer-dimer formation by capturing probes at their 5' end to a solid support. Different techniques for effecting such capture are known to the skilled artisan. One such approach is to label the 5' end of the loopback probe with biotin and to capture the probes on streptavidin coated beads. Because the probe is fixed to a solid support, formation of probe primer-dimers is sterically disfavored. After probe fixation, unbound probe is washed away. All subsequent enzymatic steps can then be effected using the probe bound to beads. If desired, however, probe may be eluted from the beads at any time.

According to another embodiment, illustrated in FIG. 2A, it is possible to further suppress the formation of spurious products by incorporating into the common primer sequences (C1 and C2) of the loopback probes one or more uridine nucleotides. As is well known in the art, some DNA polymerases, e.g., Pfu DNA polymerase, "stall" upon encountering a uracil base in the template strand. Thus, if the first extension reaction is carried out with such a DNA polymerase, then extension of probe primer-dimers and probes that have hybridized intramolecularly will fail when the polymerase reaches a uracil base; sequences complementary to C1 and C2 are therefore never generated. As a result, when common primers C1 and C2 are added to effect exponential amplification, no probe primer-dimers or intramolecularly hybridized probe is present to serve as template for the synthesis of spurious products.

If the uracil base-incorporation strategy is utilized, it will be apparent that cleavage of the cleavable site must not rely on the presence of uracil bases, because any treatment affecting uracil bases in the cleavage site would also affect uracil bases in the common primer sequences of the probe.

It will also be apparent that the second extension reaction must utilize a DNA polymerase that does not stall upon encountering a uracil base, e.g., T4, Klenow or Taq DNA polymerase, such that extension can proceed past the uracil bases to completion. If extension does not go to completion, sequence complementary to C2 will not be generated and it will not be possible to exponentially amplify the product of the extension reaction.

A non-uracil base sensitive DNA polymerase must also be used during the first extension using the C2 primer (e.g., PCR using the extension product as template) because the extended top strand still contains uracil bases in the C1 primer sequence. The presence of these uracil bases will prevent complete extension of the bottom strand using the top strand as template to generate an extension product containing sequence complementary to primer C1, which can serve as template for primer C1. In other words, if the first extension reaction using primer C2 does not use a uracil base-insensitive DNA polymerase, then it will also be impossible to effect exponential amplification.

Thus, PCR with primers C1 and C2 can be effected directly using Taq DNA polymerase, which is not sensitive to the presence of uracil bases. However, if it is desired to use Pfu DNA polymerase for PCR, it is necessary to first synthesize an extension product containing no uracil bases. As illustrated in FIG. 2B, this can be accomplished by a single extension by DNA synthesis of the top strand using C2 as primer and a uracil base-insensitive DNA polymerase, such as T4 or Klenow. After the extension step, Pfu can be used in PCR with C1 and C2 primers.

According to another embodiment, dNTPs labeled with an affinity capture moiety, e.g., biotin, are added during the second extension reaction. With the product of the second extension reaction thus labeled, it is possible to purify complete extension products away from probe primer-dimer and other failed extension products to further suppress the formation of spurious products. This can be accomplished by capturing the affinity capture moiety using the other component of the affinity capture system. If the biotin is used as the affinity capture moiety, then the biotinylated extension products can be captured with streptavidin coated beads, which are then washed to purify the captured products. Purified products can be eluted from the beads for use in subsequent steps, or beads can be added directly to reaction mixtures.

As illustrated in FIG. 2B, the step of purification by biotinylation and streptavidin capture can optionally be performed after probe cleavage, and before PCR using primers C1 and C2, or before the optional step of extension by DNA synthesis using C2 primer to remove all remaining uracil bases from the template, as discussed above.

Figure 3A:
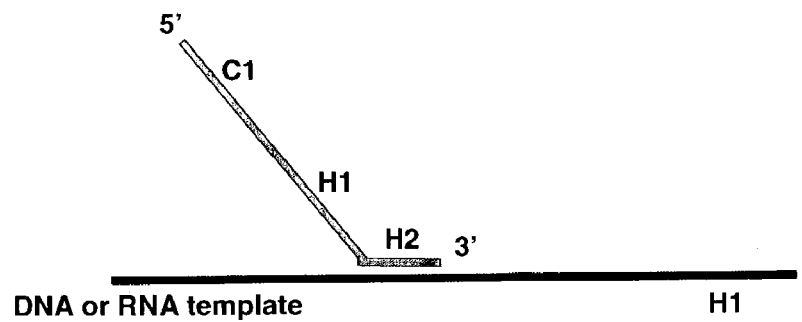
FIG. 3A illustrates an alternative embodiment of a loopback probe and the first three steps of an alternative embodiment for nucleic acid amplification according to the present invention, including probe-template hybridization, probe extension and extended probe intramolecular hybridization.
Figure 3A:
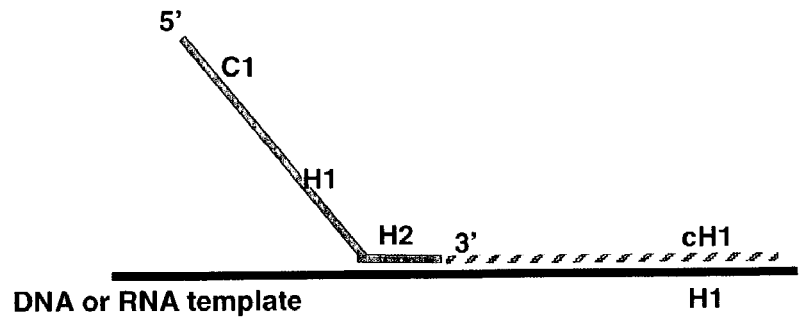
Figure 3A:
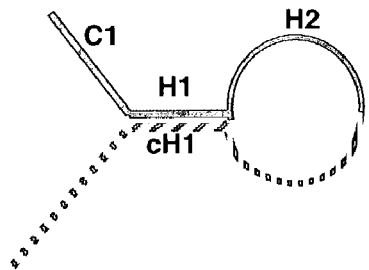

An alternative embodiment of the loopback probe is illustrated in FIG. 3A. According to this second embodiment, a loopback probe comprises a first common primer sequence (C1) at or near the 5' end of the probe, followed by a first homology region (H1) and then a second homology region (H2) proximal to the 3' end of the probe. As in the first embodiment of the loopback probe, discussed above, H2 is designed to specifically hybridize with a complementary sequence present in the template (cH2). The prior discussion pertaining to specificity of binding between probe and template homology regions for the first embodiment of the loopback probe is also relevant to its alternative embodiments.

An alternative embodiment for nucleic acid amplification using the loopback probe of FIG. 3A is also provided. According to this method, the first three steps, hybridization to template, extension and intramolecular probe hybridization, are similar to the first method illustrated in FIG. 1A and FIG. 1B and disclosed above.

However, because the alternative loopback probe of FIG. 3A contains no cleavable site, a cleavage step is omitted. Rather, as illustrated in FIG. 3B, after intramolecular hybridization between H1 and cH1 (which was generated during extension) any single-stranded tail or overhang extending past (in the 3' direction) the duplex formed between H1 and cH1 is removed by treating the probe with an exonuclease which removes unpaired nucleotides from the 3'-5' direction (e.g., exonuclease I (ExoI) or exonuclease T (ExoT)).

Figure 3B:
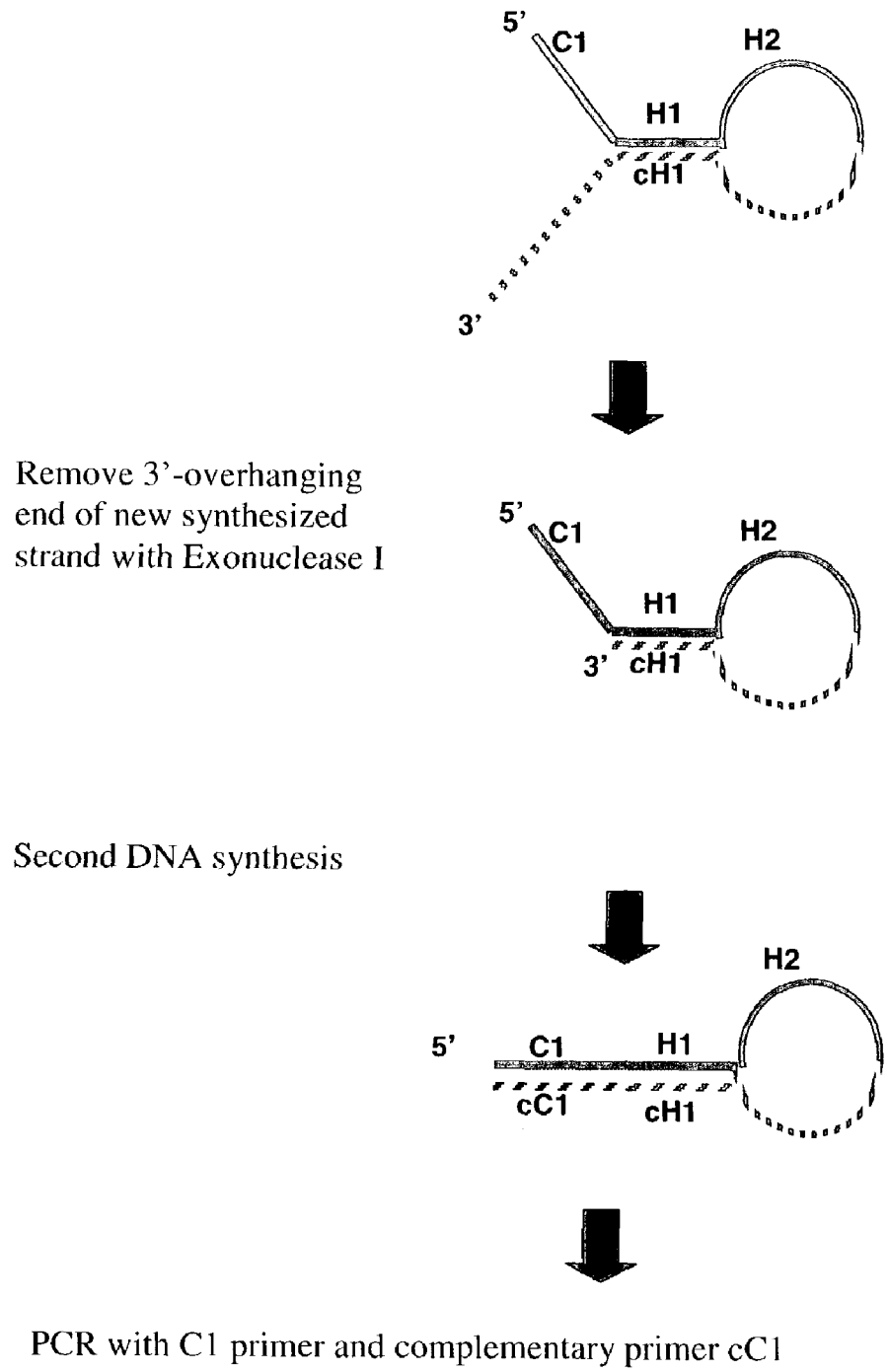
FIG. 3B illustrates a further three steps of the alternative embodiment of the method illustrated in FIG. 3A, including removal of unpaired extension product, extension using the original probe sequence as template and exponential amplification by PCR.
Figure 3B:
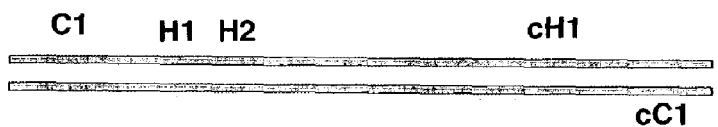

As illustrated in FIG. 3B, having removed any unpaired 3' nucleotides, a DNA polymerase is then used to extend the probe from the 3' end of cH1. This extension reaction generates a sequence complementary to the common primer sequence C1 (cC1) at or near the 3' end of the extended probe, having used the C1 sequence at or near the 5' end of the original probe as template. In an alternative embodiment, a DNA polymerase possessing a 3'-5' proofreading activity may be used to both remove the 3' tail and extend the probe.

The resultant molecule then serves as template to be amplified by PCR using a primer containing the C1 sequence and a primer containing the complement of C1 (cC1), as illustrated at the bottom of FIG. 3B.

Those optional steps to the first amplification method, disclosed above, which can be added to reduce the synthesis of spurious products can also usefully be applied in the context of the alternative embodiments of the method, such as the embodiment employing the non-cleavable loopback probe.

A third embodiment of the loopback probe is also provided which is identical or highly similar in configuration to the first embodiment illustrated in FIG. 1A, except that it lacks a cleavable site. Thus, the configuration of the probe is 5'-C1-H1-C2-H2-3'.

This probe is used in a method that share similarities to both the first and second methods of amplification disclosed above. The probe is first hybridized to template. Second, the probe is extended from H2 as primer using a DNA polymerase. Third, the extended probe is allowed to hybridize intramolecularly. Fourth, any existing 3' tail extending past the H1-cH1 duplex is removed with an exonuclease. Fifth, the self-hybridized extended probe is further extended to generate sequence complementary to the C1 common primer sequence (i.e., cC1). At this stage, the resulting molecule serves as PCR template. However, in contrast to the second method which uses for PCR primers containing C1 and cC1 sequences, respectively, PCR is effected using primers containing C1 and C2 sequences, as in the first method.

According to yet further alternative embodiments of loopback probes and methods using such probes for nucleic acids amplification, a unique identifier sequence known as a "barcode" (Bc) sequence can usefully be included in a loopback probe. An advantage of so doing is that PCR products formed using such probes can be qualitatively and quantitatively analyzed with much greater speed and efficiency as compared to traditional methods of analysis, such as direct sequencing or Southern analysis. As will be appreciated by the skilled artisan, use of barcodes in loopback probes is particularly advantageous when such probes are to be used for multiplex PCR. In this manner, efficient multiplex PCR can be coupled with multiplex identification of specific reaction products.

As known to those with ordinary skill in the art, a set of distinct barcode sequences can be designed for the purpose of uniquely identifying an equivalent number of nucleic acids, wherein each nucleic acid to be identified possesses one barcode sequence selected from among the set, thereby establishing one-to-one correspondence between a particular barcode and a particular nucleic acid.

The complement of each barcode sequence can be immobilized on a solid substrate, e.g., a glass wafer, in a predefined spatial pattern using techniques familiar to the skilled artisan. Thereafter, fluorescently labeled nucleic acids containing barcode sequences are hybridized to the sequences on the wafer, followed by detection using a laser scanner.

Because of the one-to-one correspondence between a barcodes and coded nucleic acids, qualitative measurement of the presence or absence of particular nucleic acids, and/or quantitative measurement of the amount of such nucleic acids can be inferred based upon where on the wafer fluorescence signal is detectable, coupled with knowledge of the location on the wafer of the complements of specific barcodes.

Additional discussion of barcode sequences and applications utilizing such sequences is found in, among other sources, Shoemaker et al., Nature Genet. 14(4):450-456 (1996); EP 0799897; Fan et al., Genome Res. 10:853-680 (2000); U.S. Pat. No. 6,150,516; PCT publication WO 02/059354 and PCT publication WO 02/059355, the disclosures of which are incorporated herein by reference in their entireties.

Figure 7:
FIG. 7 illustrates two embodiments of loopback probes containing barcode sequences, according to the present invention.
Figure 7:
Figure 7:
Figure 7:

With respect to the first loopback probe embodiment disclosed herein, a barcode sequence can be placed between C1 and H1 sequences. As illustrated in the top part of FIG. 7, upon use of the probe to amplify a sequence of interest in a template (sequence), a PCR product is generated having the following configuration on the top strand of the double stranded product: 5'-C1-Bc-H1-template sequence-cH2-cC2-3'.

According to an alternative embodiment, a barcode sequence can be placed between C2 and H2 of the probe. As illustrated in the bottom part of FIG. 7, upon use of this probe to amplify a sequence of interest, a PCR product is generated having the following configuration on the bottom strand: 5'-C2-Bc-H2-sequence-cH1-cC1-3'.

The compositions and methods of the instant invention can beneficially improve the performance of all applications to which conventional multiplex PCR and related methods have heretofore been put.

Thus it is possible to apply the compositions and methods of the present invention to amplify in the same reaction sequences of multiple genes from the genomic DNA of a single patient. In this manner the status of a multifactorial genetic diseases, such as cancer, can be studied.

In another embodiment, it is possible to quantify the amount of a specific nucleic acid in a sample. This includes, e.g., measuring the quantity of a particular mRNA in an RNA sample, and measuring the number of copies of an amplified oncogene in a sample of genomic DNA. It is also possible to simultaneously amplify RNA and DNA template present in the same sample using the compositions and methods of the present invention.

For purposes of template quantitation, the two homology regions of the probe, H2 and H1, are generally be chosen to be relatively close to each other and to be of similar size. As will be apparent to the skilled artisan, the detection and quantitation of amplified products can be accomplished through the use of loopback probes containing barcodes.

In yet another embodiment, splice variants present in a population of mRNA or hnRNA can be analyzed by designing loopback probes to contain H2 and H1 homology regions at exon-exon junctions or in separate exons.

The compositions and methods of the present invention may also usefully be applied to the task of SNP genotyping.

In one series of such embodiments, the probe would be designed so that its 3' end hybridizes just downstream of the template nucleotide to be interrogated. For each SNP type two reactions would be done. All variations could be formatted to 4 different types: for example A/G, A/C, A/T, and G/C SNPs. Therefore all SNPs could be interrogated in eight reactions. In the example of an A and G SNP, one reaction is set up with a deoxy G and a dideoxy A and another with a dideoxy G and a deoxy A. After extending the one base, apyrase is used to destroy the nucleotides, and then all 4 nucleotides are added and the amplification procedure is followed as has been described above.

The homology regions used in such SNP genotyping assays are likely close to each other and generate small and similar sizes. A barcode or tag could be incorporated into the probe to allow the detection for the presence or absence of that specific sequence in that specific reaction. If the SNP genotyping assay further utilizes a barcode chip, the 8 reactions could be consolidated. For example, the reaction containing deoxy A and dideoxy G and that of deoxy A and dideoxy C could be combined. Indeed potentially the consolidation could reduce the number of samples to be hybridized on chips to two reactions.

It is also possible to perform SNP genotyping on RNA, using the techniques disclosed herein, in order to quantitate expression of each of the two different alleles. Again, such genotyping assays can be performed in multiplex fashion, and can incorporate the use of barcodes for detection purposes.

In another aspect, the present invention also provides methods of nucleic acid amplification using self-priming probes capable of sustained amplification.

In this method, single molecule probes are provided that both prime and continue the amplification, without the need for common primers. Because the probes in these embodiments are used for amplification, the amount used will typically be considerably more than the amounts of probe used in the above-described methods, and will most often be in the fmole or greater range.

Figure 8B:
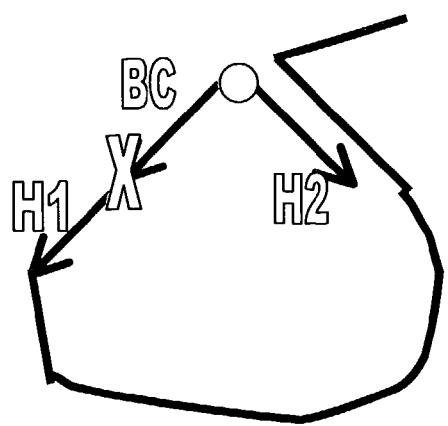
FIG. 8B illustrates three additional steps of a method using the probe of FIG. 8A for nucleic acid amplification.
Figure 8B:
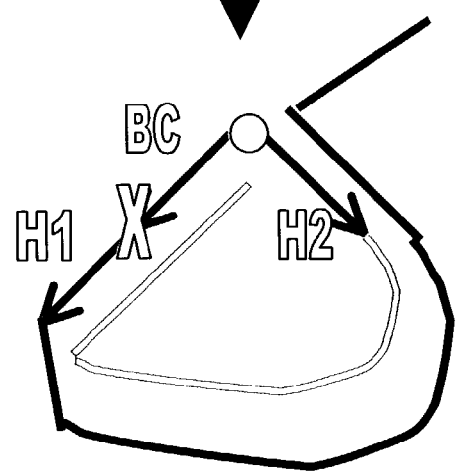
Figure 8B:
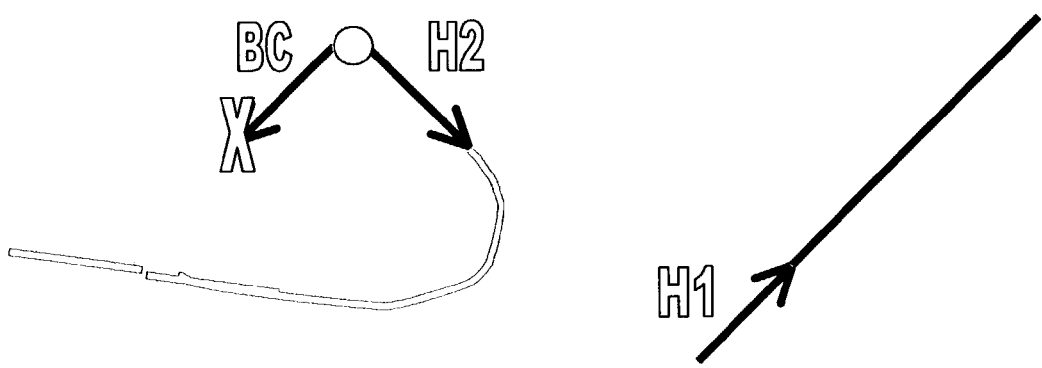

As schematically depicted in FIGS. 8A-8C, the method utilizes probes that have dual polarity, where both ends of the probe are 3' ends and there is a change of polarity between the ends of the probe. One arm of the probe carries a first homology region (H1), and the other arm carries a specific sequence (BC) followed by a second homology region (H2). The specific sequence can be, e.g., a barcode sequence, but can also be, e.g., another homology region. A cleavable site (X) separates the specific sequence (BC) and second homology region (H2).

The cleavable site is such that it can be generated by DNA polymerization. For example, the cleavable site can be a site for a nicking restriction enzyme like BstNBI, BstSEI, or Bst9I, all active at elevated temperature.

Alternatively, one could use a restriction enzyme, but limit the digestion to one strand only. One way to do this is to utilize in the DNA synthesis one or more nucleotide with thiophosphate leading to inhibition of digestion of that strand. Multiple enzymes are known to function in this fashion at high temperatures, like Bso BI. At least one enzyme (Bsm I) is known to nick the strand with thiophosphate, making it possible to do the DNA synthesis with regular nucleotides and putting thiophosphate in the probe. The probe could be immobilized in order to minimize any potential for primer dimer. The immobilization could be achieved for example, by capturing a biotin molecule located on the probe with streptavidin beads. A suitable position to incorporate biotin into the probe would be at or near the site of polarity change.

As shown in FIG. 8A, the first step is hybridization of template DNA to the first homology region (H1) of the probe, followed by extension of the probe from the first homology region (H1) to create the "first strand."

Denaturation is then followed by hybridization, under conditions that promote self-hybridization, such as relatively short hybridization times, low salt and/or dilution.

"Second strand" synthesis is then performed, extending from the second homology region (H2), followed by nicking of the cleavable site (X), and denaturation, to yield the "first strand" containing the first homology region (H1), the target sequence complement, and the second homology region (H2) complement, and the "second strand" containing the specific sequence (BC), polarity shift region, second homology region, target sequence, first homology region (H1) complement, and specific sequence (BC) complement.

The nicking step typically uses an enzyme that works at elevated temperatures, permitting nicking to be performed in the same step as DNA polymerase extension.

The two strands generated from the above steps, i.e., the first and second strands, are capable of exponential amplification. The second synthesized strand is capable of self-hybridization at the specific sequence (BC), and subsequent extension to yield another copy of the first strand that can again be released by nicking the cleavable site. The original first strand is capable of hybridizing to a new probe that can be extended to generate a strand that can in the next cycle self hybridize and serve as a template for an extension reaction. The strand being released from the probe and can be used in downstream applications with the caveat that it does not carry a specific sequence (BC) or barcode. The amplified strand connected with the probe does carry the specific sequence (BC) or barcode, which can be utilized in downstream detection schemes. In some applications, the presence of the non-biological polarity change in the probe may be less than desirable. In these cases, the probe can be designed to carry a cleavable site like a uracil base or a ribose base to release the amplified strand from the probe.

In this method there is the possibility of undesired hybridization of a strand released by nicking to a new probe. Exponential growth of a spurious product will occur only if the hybridization is to the probe arm that can be nicked. This amplification requires a bimolecular hybridization in every cycle. To combat this potential background, the homology region (H1) on the arm that can be nicked is made to be short and have a low melting temperature. In such a situation, the bimolecular hybridization is not likely to occur suppressing the likelihood of a spurious product. The intramolecular hybridization of H1 to its complement would still occur given the high effective concentration of the two sequences on the same probe molecule. In later cycles the intramolecular hybridization would be even more favored as the barcode is added to H1 to form a longer complementary region.

One way to use this method is to start by linear amplification by only allowing for self hybridization (e.g. by dilution) and extension after generation of the second strand. After enrichment by the linear amplification of the proper product, but not primer-dimer or other spurious products, the exponential phase can be started. Immobilization of the probes can greatly minimize primer-dimer formation and may be used in addition to, or instead of, the initial linear amplification method. The main background possible in this scheme is self priming. Care should be taken to assure no self priming between the two 3' ends. A self priming event between a 3' end of an arm of a probe and the middle of the second probe does not allow exponential growth, but a self priming event between the 3' ends of the two arms of the probe will amplify exponentially.

A variation on the above method is to depend solely on the linear amplification. This can be suitable for example in nucleic acid quantitation. One way to make the system amplify in a linear manner is to make the site that can be nicked at the end of the arm. In such a case the amplification occurs by self hybridization and nicking. The released molecule is able to prime a new probe but the resultant extension cannot self hybridize. A convenient nickable site is a ribose residue. The thermostable RNAse A or RNAse T1 (depending on the specific ribose residue), can cleave an extended ribose that can then be extended in the next cycle.

In the above methods, the amplified strands are released from the probe by nicking and denaturation steps. However, alternative methods of releasing the amplified strand are also contemplated. It is further contemplated that the synthesized and released strand can be an RNA strand.

For example, a sequence for T7 polymerase (or T3 or SP6) can be placed upstream of the sequence of the barcode on a probe that does not contain a nickable site. The first and second strand synthesis procedure can be otherwise performed as described above. The double stranded T7 promoter sequence can be used for RNA transcription to generate many copies of one of the two strands. In such a method, the amplification is linear.

In cases where further amplification is required, a reverse transcriptase can be used to generate the complement to the RNA transcript, which is then able to hybridize with new probe molecules. A denaturation step can be done which will allow the release of the RNA strand from the probe followed by a self hybridization and DNA polymerization step to generate double stranded molecule with double stranded T7 promoter sequence. A new round of RNA transcription generates more RNA transcripts than in the initial transcription as the number of template molecules is larger. As T7 polymerase is not heat stable, additional polymerase is added at this step, although suitable thermostable RNA polymerase would also be of utility. Alternatively, instead of using heat to denature the RNA/DNA duplex, RNAse H can be used to eliminate the RNA strand in the hybrid. For each RNA strand being degraded there is a generation of a new double stranded T7 polymerase sequence that is produces many copies of that RNA strand.

The following examples illustrate steps of the methods of the present invention. The following examples are offered by way of illustration and not by way of limitation.

EXAMPLE 1

Extension of a Loopback Probe Hybridized to a DNA Template and a RNA Template

A 130 nucleotide loopback probe, called A1, is synthesized with the following sequence:

[SEQ ID NO:1]
TTGTCGAACAGTCCACGAGGTCTCTAGTCCGAATTGTTTCATCATCGTTA

UUACGTAGCTGTAAAACGTCGGCCAGTGCTATTCGCTGGAGTTCGCACGC

TATATTTAAAAGCATCACCAGAAGAAACAG.

Figure 4A:
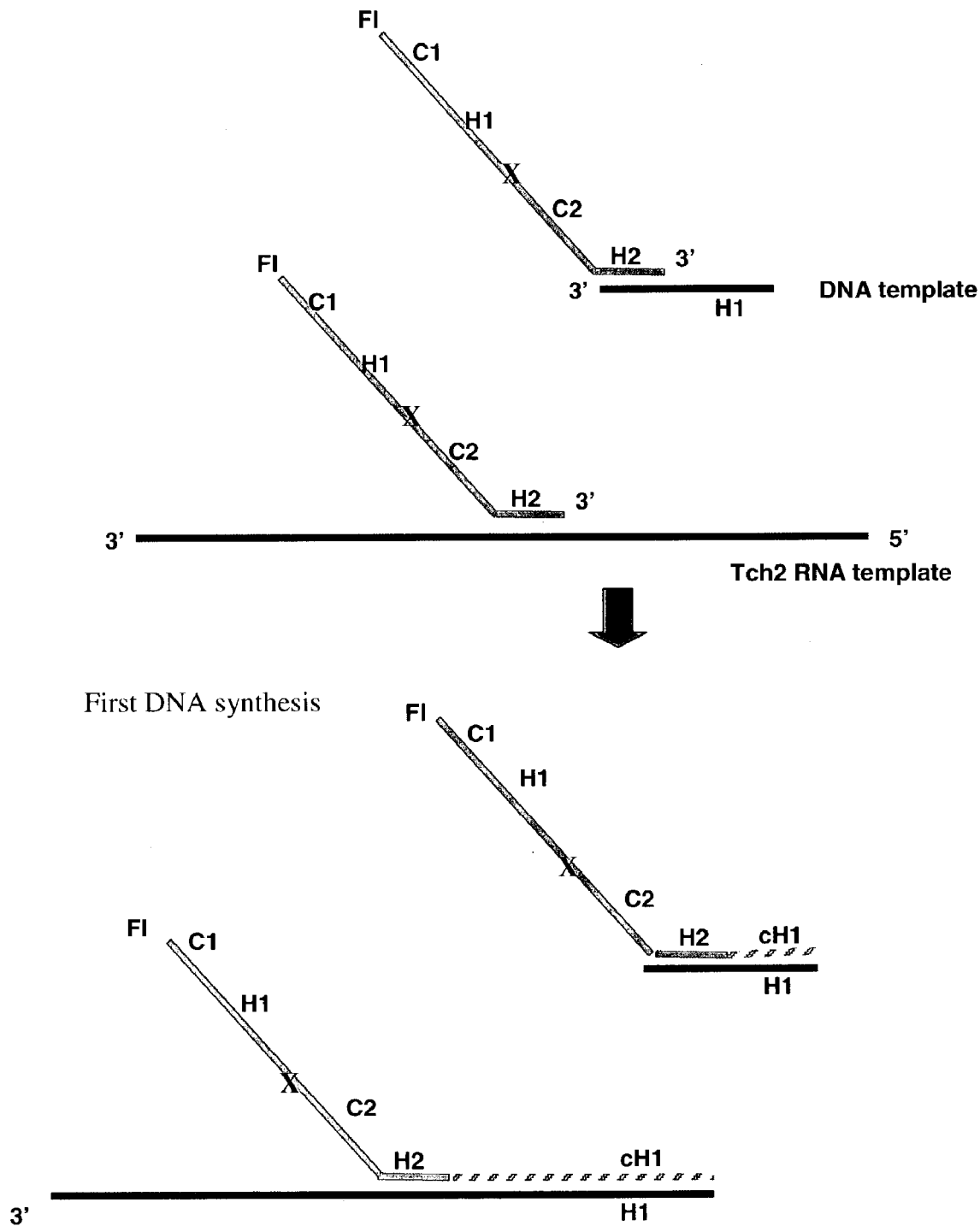
FIG. 4A illustrates the loopback probe and method steps used in the experiments of Example 1.

A1 is labeled at its 5' end with the fluorescent dye Cy3 (denoted in FIG. 4A by "Fl" at the 5' of the probe). The sequence of C1 is GTCCACGAGGTCTCTAGTC [SEQ ID NO: 2]. The sequence of C2 is TGTAAAACGTCGGCCAGTGC-TATTC [SEQ ID NO: 3]. The sequence of H1 is CGAAT-TGTTTCATCATCGTTA [SEQ ID NO: 4]. The sequence of H2 is AGCATCACCAGAAGAAACAG [SEQ ID NO: 5]. Two uracil bases follow immediately at the end of H1 and serve as the cleavage site. After synthesis, A1 is then gel purified.

Extension of Probe A1 Using a DNA Template:

Probe A1 is mixed with the DNA template in reaction buffer to a final concentration of 10 nM and 50 nM, respectively. Template DNA is a 41 nucleotide cDNA fragment called cpm39-60. The sequence of cpm39-60 is CGAAT-TGTTTCATCATCGTTACTGTTTCTTCTGGTGATGCT [SEQ ID NO: 6]. Reaction buffer (1×) contains 20 mM Tris HCl (pH 8.3), 25 mM KCl, 10 mM MgCl, 1 mM DTT and dNTPs at 0.2 µM each. The mixture is then incubated at 80° C. for 2 min and then at 46° C. for 30 min at to allow A1 to specifically hybridize to template. H2 in probe A1 hybridizes with the 20 nucleotides at the 3' end of cmp39-60, thereby leaving 20 nucleotides of template to be read by the DNA polymerase. Probe A1 hybridized to template is illustrated in FIG. 4A.

To the mixture is then added 5 units of the Stoffel fragment of AmpliTaq DNA polymerase (Perkin Elmer, Inc.) followed by mixing. The extension reaction is then allowed to proceed with aliquots being taken at 10, 20 and 40 minutes. The reaction products are then analyzed by electrophoresis using a denaturing 7M urea polyacrylamide gel. Bands of reaction product are detected by scanning the gel with a fluorescent scanner. Probe A1 extended on the template is illustrated in FIG. 4A.

Figure 4B:
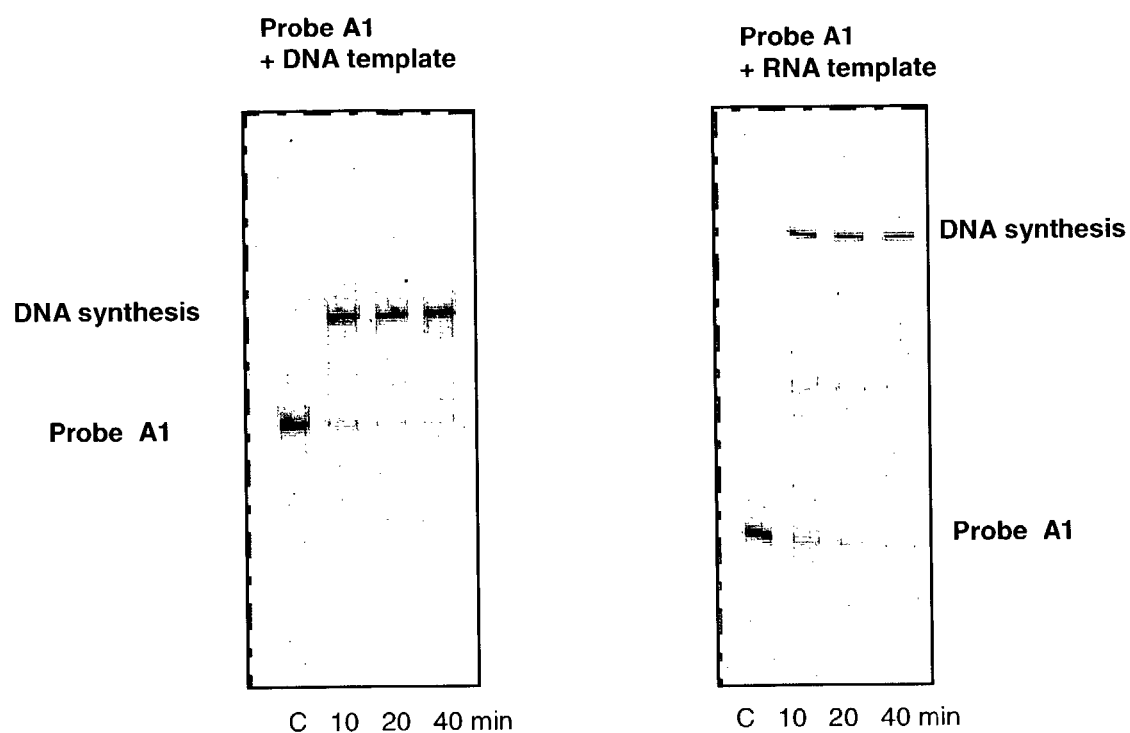
FIG. 4B illustrates the results of the experiments of Example 1.

Results of the extension reaction using DNA template are shown in the left half of FIG. 4B. In lane 1 is unreacted probe A1. In lanes 2-4 is probe that has been extended an additional 20 nucleotides using the DNA as template, causing the extended probe to run at lower mobility compared to unreacted probe. The highest mobility band in lanes 2-4 corresponds to unreacted probe A1. According to the results of this experiment, extension of probe A1 is nearly complete by 10 minutes.

Extension of Probe A1 Using an RNA Template:

Probe A1 is hybridized to the 350 nucleotide Tch2 RNA transcript as described above. The 3' end of probe A1 is located 60 nucleotides from 5' end of the RNA template. Probe A1 hybridized to template is illustrated in FIG. 4A. Superscript II reverse transcriptase (Invitrogen, Inc.) is then added to reaction mixture to effect extension of the probe.

Probe A1 extended on the template is illustrated in FIG. 4A. Reaction products are then analyzed as described above.

Results of the extension reaction using an RNA template are shown in the right half of FIG. 4B. In lane 1 is high mobility unreacted probe A1. The reaction products analyzed in lanes 2-4 demonstrate that the probe is extended 60 nucleotides by reverse transcriptase, resulting in lower mobility bands. As with the DNA template, the extension reaction is substantially complete by 10 minutes.

EXAMPLE 2

Cleavage of a Loopback Structure Having Uracil Bases at the Cleavage Site

To confirm the cleavage step, two loopback probes, called 2B and 2A, respectively, are synthesized and gel purified. Both probes are labeled at their respective 5' ends with the fluorescent dye Cy3 (denoted in FIG. 5A and FIG. 6A by "Fl" at the 5' end of the probes). The sequence of 2B is:

```
                                             [SEQ ID NO:7]
CATGCTGTCAGTACCACCATCACAGGTTGGTCTGGTCTCUUACCACCTTC

TCACGGCTCAACGTTCCTATTCGGTTTTTTTGCAAATGTTATCGAGGTCC

GGCGAGACCAGACCAACCTGTGATTTTTT.
```

The sequence of 2A is:

```
                                             [SEQ ID NO:8]
CATGCTGTCAGTACCACCATCACAGGTTGGTCTGGTCTCTTACCACCUUC

TCACGGCTCAACGTTCCTATTCGGTTTTTTTGCAAATGTTATCGAGGTCC

GGCGAGACCAGACCAACCTGTGATTTTTT.
```

Both 2B and 2A contain a 5' homology region, called H1, and its complement, called cH1, near the 3' end of the each probe. The sequence of H1 is: TCACAGGTTGGTCTGGTCTC [SEQ ID NO: 10]. The sequence of cH1 is: GAGACCAGAC-CAACCTGTGA [SEQ ID NO: 9]. The principal difference between probes 2B and 2A is that probe 2B has two uracil bases present immediately after the H1 sequence, whereas probe 2A has two uracil bases separated by eight bases from the end of the H1 sequence.

Figure 5A:
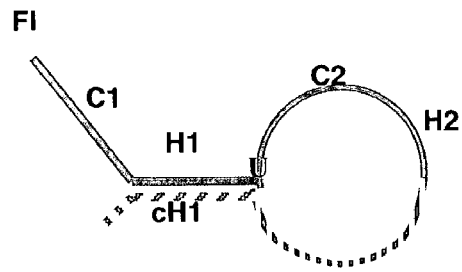
FIG. 5A illustrates the loopback probes (structures 2A and 2B) and method steps used in the experiments of Example 2.
Figure 5A:
Figure 5A:
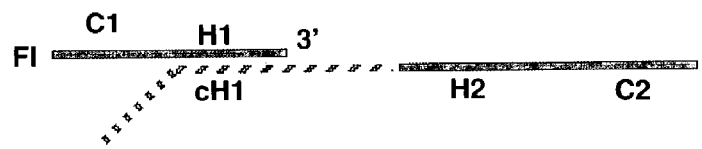
Figure 5A:
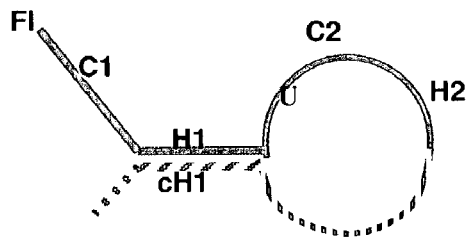
Figure 5A:
Figure 5A:
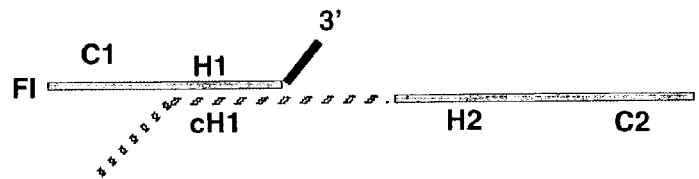

Separately, probes 2B and 2A are mixed with reaction buffer to a final probe concentration of 20 nM and buffer concentration of 1×(20 mM Tris HCl, pH 8.3, 25 mM KCl, 10 mM MgCl, 1 mM DTT and each of the four dNTPs to 0.2 µM). The mixtures are then heated to 80° C. for 2 min followed by 46° C. for 5 min to allow H1 and cH1 to hybridize to each other, thereby forming loopback structures, which are illustrated in FIG. 5A.

Uracil-DNA glycosylase (UDG) (New England Biolabs, Inc.) is then added to the reactions at a final concentration of 0.03 units/uL after which the reaction is incubated at 37° C. for 20 min to allow the UDG to remove the uracil bases from the loopback structures, thereby creating apurinic (AP) sites.

Five different AP-cleaving enzymes, including EndoIV (Trevigen, Inc.), APEI (Trevigen, Inc.), ExoIII (United States Biological, Inc.), EndoIII (New England Biolabs, Inc.) and Fpg (New England Biolabs, Inc.) are then tested for their ability to cleave the loopback probes 2B and 2A. In separate reactions, each enzyme is added and incubated at 37° C. to effect cleavage.

As noted, the uracil bases of probe 2B follow immediately after H1. Thus, if cleavage is effected, it will occur immediately after the duplex formed by H1 and cH1 and at the beginning of the single-stranded loop between H1 and cH1 leaving no 3' overhang after the duplex. The uracil bases of probe 2A, in contrast, follow by 8 nucleotides the end of H1. Thus, if cleavage is effected, it will occur further into the single-stranded loop and leave an 8 nucleotide single-stranded tail at the 3' end of H1. The alternative cleavage structures are illustrated in FIG. 5A.

During the cleavage reactions, aliquots are removed and the reaction products are analyzed by denaturing gel electrophoresis on a denaturing 7M urea polyacrylamide gel. Bands of reaction product are detected by scanning the gel in a fluorescent scanner.

Figure 5B:
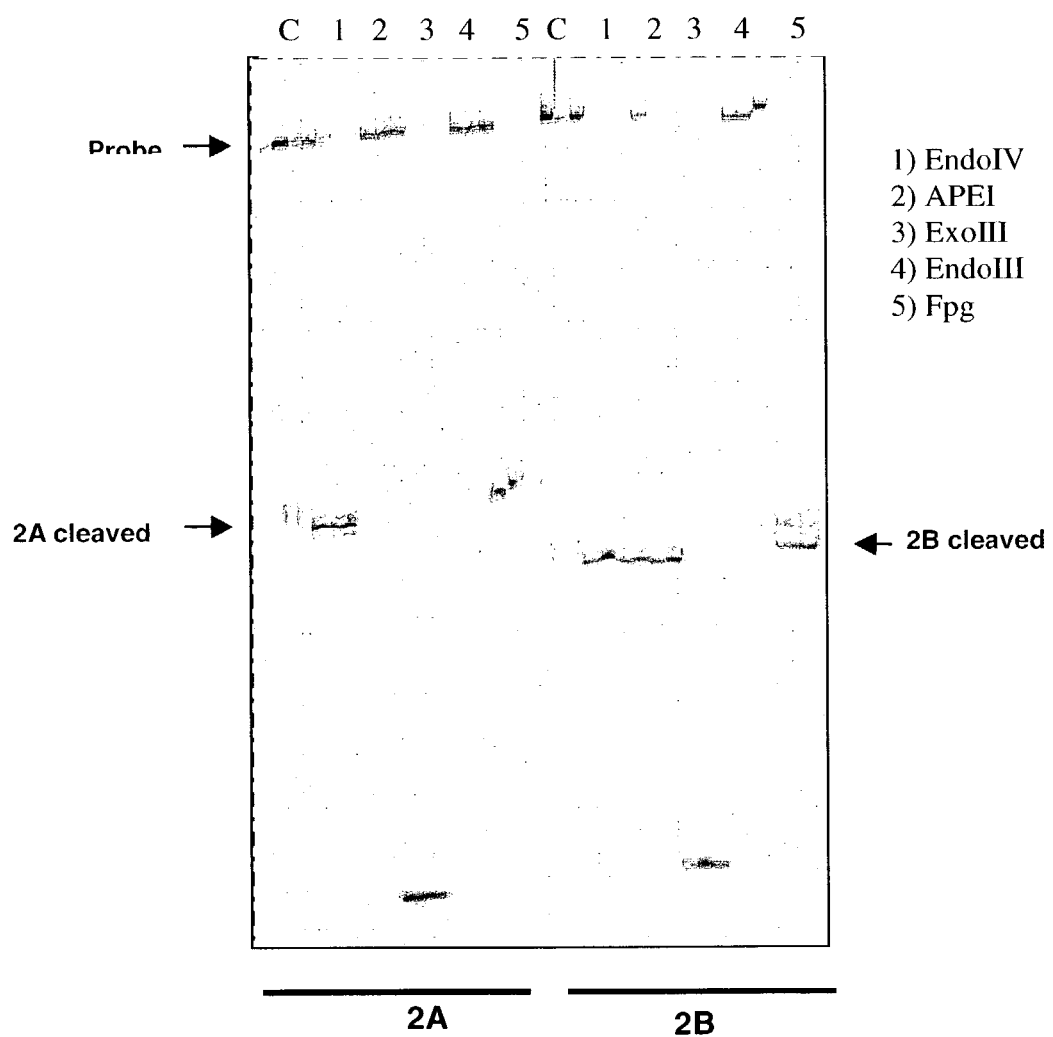
FIG. 5B illustrates the results of the experiments of Example 2.

Results of these experiments are shown in FIG. 5B. Unreacted probe 2A appears in lane "C" on the left half of FIG. 5B. Unreacted probe 2B appears in lane "C" on the right half of FIG. 5B. Both probes migrate in the gel at relatively low mobility. Lanes numbered 1-5 show the results of attempted cleavage with enzymes EndoIV, APEI, ExoIII, EndoIII and Fpg, respectively. As expected, ExoIII completely degraded probe 2B (lane 3, right side of FIG. 5B). Probe 2A was also degraded (lane 3, left side of FIG. 5B), possibly due to single-stranded exonuclease contamination in the commercial ExoIII preparation used in the experiments.

For probe 2A in contrast, EndoIV (lane 1) and Fpg (lane 5), but not APEI (lane 2) or EndoIII (lane 4), were successful in increasing the mobility of the fluorescent band without completely degrading the probe, indicating that EndoIV and Fpg cleaved probe 2A at the AP-site.

With respect to probe 2B, however, three enzymes successfully increased the mobility of the probe, indicating their ability to cleave the AP-site, including EndoIV, APEI and Fpg. Again, EndoIII could not cleave the loopback probe.

Note that mobility of cleaved probe 2A is slightly lower than that of cleaved probe 2B, which is consistent with cleavage of probe 2A leaving 8 additional nucleotides at the 3' end of the H1 as compared to cleavage of probe 2B.

EXAMPLE 3

Extension of a Cleaved Loopback Structure

Probe 2A is formed into a loopback structure and cleaved with UDG and EndoIV as described above in Example 2.

Thereafter, samples of cleaved probe 2A are separately treated with three different DNA polymerases, with or without the addition of ExoI, to effect extension from the 3' of the cleaved probe. The DNA polymerases tested are the Klenow fragment of DNA polymerase I (New England Biolabs, Inc.) (incubation at 37° C.), the Stoffel fragment of AmpliTaq DNA polymerase (Perkin Elmer, Inc.) (incubation at 50° C.) and Pfu DNA polymerase (Stratagene, Inc.) (incubation at 50° C.).

Figure 6A:
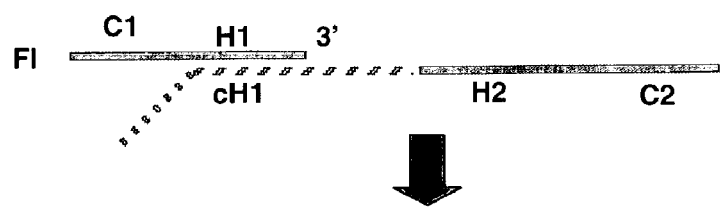
FIG. 6A illustrates the loopback probe (structure 2A) and method steps used in the experiments of Example 3.
Figure 6A:
Figure 6A:
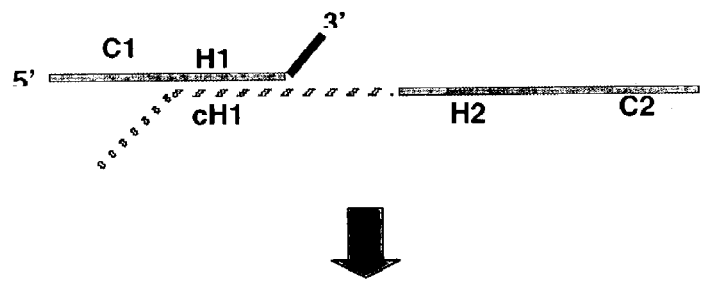
Figure 6A:
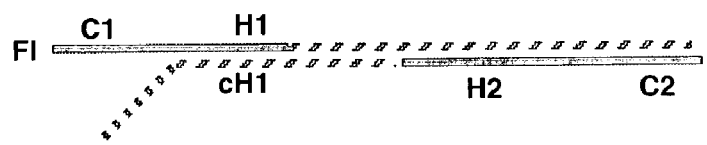

Schematics of the cleaved and extended probes are illustrated in FIG. 6A.

Following the reactions, aliquots are removed and the reaction products analyzed by denaturing gel electrophoresis on a 7M urea polyacrylamide gel. Bands of reaction products are detected by scanning the gel with a fluorescent scanner.

Figure 6B:
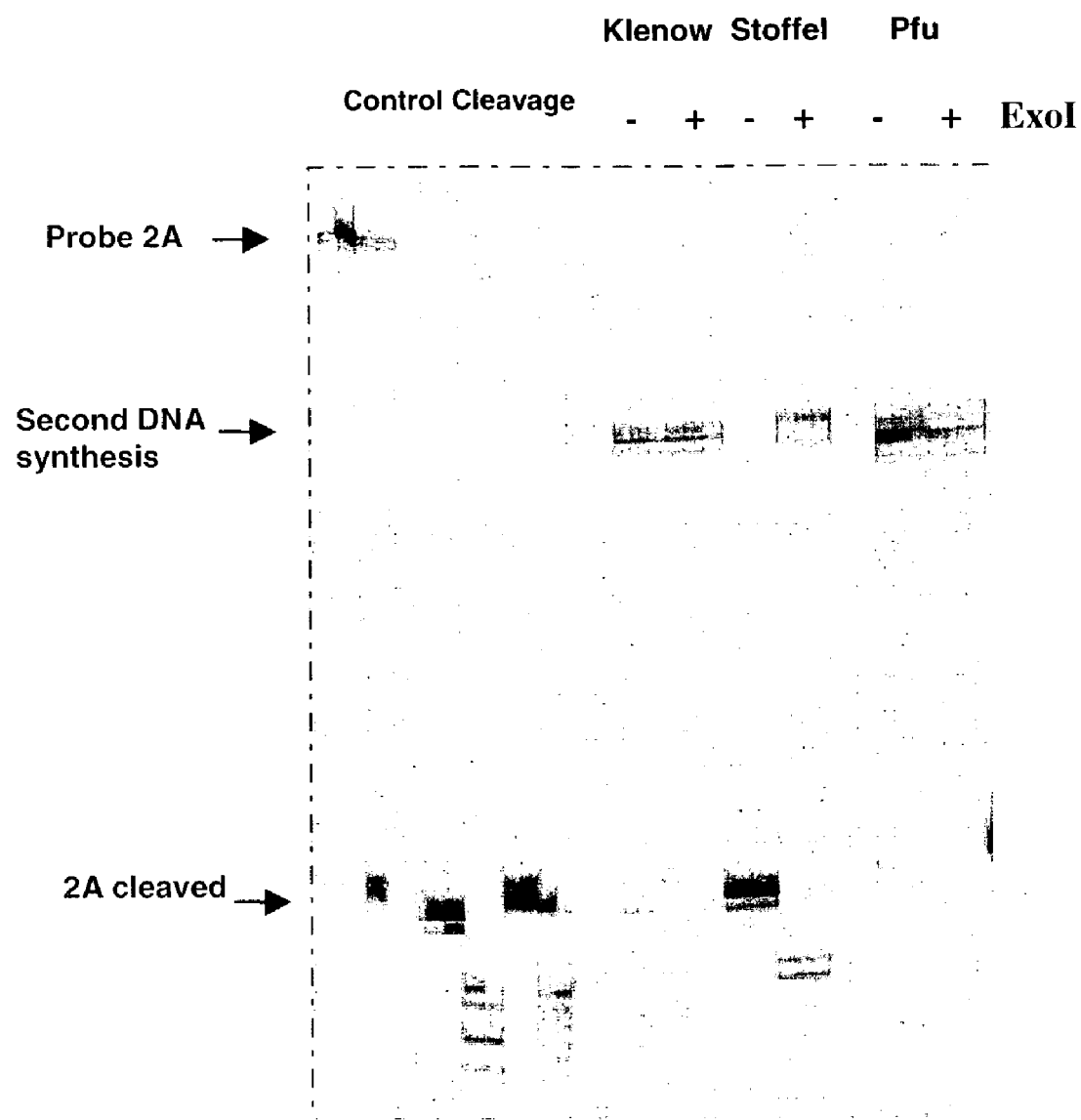
FIG. 6B illustrates the results of the experiments of Example 3.

Results are shown in FIG. 6B. In the left portion of FIG. 6B are the results of control reactions. As in Example 2, uncleaved probe 2A migrates at low mobility, whereas cleaved probe migrates at higher mobility because the fragment with the fluorescent label is smaller after cleavage.

As noted above, cleavage of probe 2A leaves an 8 nucleotide 3'-overhang following the H1-cH1 duplex. Unless the single-stranded overhang is removed, the cleaved probe cannot be extended. The results using Klenow enzyme indicate that the 3'-5' single-stranded exonuclease activity possessed by Klenow enzyme is able to remove the overhang after which the enzyme's DNA polymerase activity successfully extended the cleaved probe from the end of H1. FIG. 6B shows that after cleavage and extension with Klenow, the fluorescently labeled fragment migrates with lower mobility compared with untreated cleaved probe, as expected. Presence of ExoI ("+" lane) is redundant with respect to Klenow alone ("−" lane).

In contrast, treatment of cleaved probe with the Stoffel fragment alone ("−" lane) is not effective to extend because the Stoffel fragment lacks any 3'-5' single-stranded exonuclease activity. Addition of ExoI ("+" lane) remedies this by first removing the 3'-overhang, allowing the DNA polymerase activity of the Stoffel fragment to then extend from H1.

Lastly, Pfu polymerase, which like the Klenow fragment possesses a 3'-5' single-stranded exonuclease activity, is competent to remove the 3' cleavage overhang and to extend the probe using H1 as a primer (compare "−" lane to "+" lane).

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. A method of amplifying a nucleic acid template, comprising the steps of:
    (a) contacting a linear amplification molecule to a nucleic acid template under conditions that support specific hybridization between one end of the linear amplification molecule and the template, the linear amplification molecule having a homology region and a cleavable site, wherein said homology region and said cleavable site are between a first primer region and a second primer region, wherein said cleavable site is located 3' of said homology region, and wherein said homology region is between 15 and 100 nucleotides in length and has the same sequence as a sequence in the nucleic acid template,
    (b) adding sequentially to said linear amplification molecule at the end hybridized to said template, nucleotides complementary to corresponding nucleotides present in said template, whereby an extended linear amplification molecule containing a newly-added sequence capable of specific hybridization to the homology region in the linear amplification molecule is formed,
    (c) incubating said extended linear amplification molecule under conditions that support its specific intramolecular hybridization, whereby a double-stranded intramolecular hybridization region is formed between the homology region and the newly-added sequence capable of specific hybridization to the homology region,
    (d) cleaving said extended linear amplification molecule at the cleavable site, whereby a first fragment and a second fragment of said extended linear amplification molecule are formed, wherein said first fragment comprises said first primer region and said second fragment comprises said second primer region, and whereby said first fragment contacts said second fragment along said intramolecular hybridization region;
    (e) adding sequentially to said first fragment at the end newly created by said cleavage step one or more nucleotides complementary to corresponding nucleotides present in said second fragment, whereby an extended first fragment of the linear amplification molecule is formed; and
    (f) amplifying the extended first fragment of the linear amplification molecule by primers specific for the first and second primer regions to amplify the nucleic acid template.

2. The method of claim 1, wherein said step of amplifying is effected using the polymerase chain reaction.

3. The method of claim 1 further comprising the step of eliminating unhybridized linear amplification molecules.

4. The method of claim 3, wherein said step of eliminating unhybridized linear amplification molecules is effected using an exonuclease.

5. The method of claim 1, wherein said cleavable site of said linear amplification molecule comprises a uracil base.

6. The method of claim 5, wherein step (b) is effected using a DNA polymerase that stalls at a uracil base.

7. The method of claim 1, wherein said extended first fragment of the linear amplification molecule of step (e) comprises an affinity capture moiety.

8. The method of claim 7, wherein said affinity capture moiety is a biotinylated nucleotide.

9. The method of claim 8, further comprising the step of contacting said extended first fragment of the linear amplification molecule with a biotin-binding moiety.

10. The method of claim 9, wherein said biotin-binding moiety is selected from the group consisting of: avidin, streptavidin, biotin-specific antibody.

11. The method of claim 1, wherein said linear amplification molecule comprises an oligonucleotide.

12. The method of claim 11, wherein said oligonucleotide comprises deoxyribonucleic acid.

13. The method of claim 1, wherein said linear amplification molecule comprises a fluorescent moiety.

14. The method of claim 1, wherein said template is selected from the group consisting of: DNA, plasmid DNA, genomic DNA, viral DNA, bacterial DNA, nuclear DNA, mitochondrial DNA, cellular DNA, RNA, mRNA, hnRNA, rRNA, viral genomic RNA.

15. The method of claim 1, wherein said steps of adding nucleotides sequentially are effected using a DNA polymerase.

16. The method of claim 1, wherein said step of cleavage is effected using one or more enzymes.

17. The method of claim 1, wherein said predetermined site of cleavage is an apurinic site.

18. The method of claim 1, wherein said step of cleavage is effected using a chemical agent.

19. The method of claim 1, further comprising the step of analyzing said amplified nucleic acid template.

20. A method of simultaneously amplifying multiple nucleic acid templates, comprising the steps of:

(a) contacting linear amplification molecules to nucleic acid templates under conditions that support specific hybridization between one end of a linear amplification molecule and its respective nucleic acid template, each linear amplification molecule having a homology region and a cleavable site, wherein said homology region and said cleavable site are between a first primer region and a second primer region, wherein said cleavable site is located 3' of said homology region, and wherein said homology region is between 15 and 100 nucleotides in length and has the same sequence as a sequence in the nucleic acid template;

(b) adding sequentially to each linear amplification molecule at the end hybridized to its respective nucleic acid template nucleotides complementary to corresponding nucleotides present in said template, whereby an extended linear amplification molecule containing a newly-added sequence capable of specific hybridization to the homology region in the linear amplification molecule is formed;

(c) incubating the extended linear amplification molecules under conditions that support their specific intramolecular hybridization, whereby double-stranded intramolecular hybridization regions are formed, wherein one of the strands of each of such regions comprises nucleotides newly added in step (b);

(d) cleaving the extended linear amplification molecules at the cleavable site, whereby a first fragment and a second fragment of each extended linear amplification molecule are formed, wherein said first fragment comprises said first primer region and said second fragment comprises said second primer region, and whereby each first fragment contacts its respective second fragment along the intramolecular hybridization region;

(e) adding sequentially to each first fragment at the end newly created by said cleavage step one or more nucleotides complementary to corresponding nucleotides present in its respective second fragment, whereby an extended first fragment of the linear amplification molecule is formed; and (f) amplifying the extended first fragments of the linear amplification molecules by primers specific for the first and second primer regions to amplify the multiple nucleic acid templates.

21. The method of claim 20 wherein said step of amplifying is effected using a polymerase chain reaction.

22. The method of claim 20 further comprising the step of eliminating unhybridized linear amplification molecules.

23. The method of claim 22, wherein said step of eliminating unhybridized linear amplification molecules is effected using an exonuclease.

24. The method of claim 20, wherein said cleavable site of said linear amplification molecules comprises a uracil base.

25. The method of claim 24, wherein step (b) is effected using a DNA polymerase that stalls at a uracil base.

26. The method of claim 20, wherein said extended first fragments of the linear amplification molecules of step (e) each comprise an affinity capture moiety.

27. The method of claim 26, wherein said affinity capture moiety is a biotinylated nucleotide.

28. The method of claim 27, further comprising the step of contacting said extended first fragments of the linear amplification molecules with a biotin-binding moiety.

29. The method of claim 28, wherein said biotin-binding moiety is selected from the group consisting of avidin, streptavidin, and biotin-specific antibody.

30. The method of claim 20 wherein each of said linear amplification molecules has a distinct barcode sequence disposed between said homology region and said first primer region.

31. The method of claim 30 wherein each of said barcode sequences has a one-to-one correspondence with a nucleic acid template of said multiple nucleic acid templates.

* * * * *